US006689932B2

(12) United States Patent
Kruchoski et al.

(10) Patent No.: US 6,689,932 B2
(45) Date of Patent: Feb. 10, 2004

(54) ABSORBENT ARTICLES WITH SIMPLIFIED COMPOSITIONS HAVING GOOD STABILITY

(75) Inventors: Benjamin Joseph Kruchoski, Neenah, WI (US); Michael Brent Kottek, Neenah, WI (US); Duane Gerard Krzysik, Appleton, WI (US); Corey Thomas Cunningham, Larsen, WI (US); Lewis Preole Orchard, IV, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 122 days.

(21) Appl. No.: 10/027,264

(22) Filed: Dec. 21, 2001

(65) Prior Publication Data

US 2002/0128621 A1 Sep. 12, 2002

Related U.S. Application Data

(63) Continuation-in-part of application No. 09/746,880, filed on Dec. 22, 2000.

(51) Int. Cl.[7] ................................................ A61F 13/15
(52) U.S. Cl. ...................................................... 604/360
(58) Field of Search ................................ 604/359, 360, 604/367

(56) References Cited

U.S. PATENT DOCUMENTS

| 3,305,392 | A | 2/1967 | Britt |
| 3,489,148 | A | 1/1970 | Duncan et al. |
| 3,585,998 | A | 6/1971 | Hayford et al. |
| 3,724,465 | A | 4/1973 | Duchane |
| 3,756,238 | A | 9/1973 | Hanke |
| 3,814,101 | A | 6/1974 | Kozak |
| 3,821,350 | A | 6/1974 | Suchane |
| 3,881,488 | A | 5/1975 | Delanty et al. |
| 3,896,807 | A | 7/1975 | Buchalter |
| 3,902,493 | A | 9/1975 | Baier et al. |
| 4,040,857 | A | 8/1977 | Lissant |
| 4,100,324 | A | 7/1978 | Anderson et al. |
| 4,164,563 | A | 8/1979 | Chang |
| 4,273,786 | A | 6/1981 | Kraskin |
| 4,343,783 | A | 8/1982 | Hooper et al. |
| 4,355,020 | A | 10/1982 | Kuy |
| 4,355,046 | A | 10/1982 | Suess |
| 4,556,560 | A | 12/1985 | Buckingham |
| 4,604,313 | A | 8/1986 | McFarland et al. |
| 4,613,447 | A | 9/1986 | Hara et al. |
| 4,623,339 | A | 11/1986 | Ciraldo et al. |

(List continued on next page.)

FOREIGN PATENT DOCUMENTS

| CA | 2019557 | 12/1990 |
| DE | 35 36 318 A1 | 4/1987 |
| DE | 41 36 540 A1 | 5/1992 |

(List continued on next page.)

OTHER PUBLICATIONS

Patent Abstracts of Japan 02043265 A: Description of Masaru et al. , "Thixotropic Semisolid Composition."

(List continued on next page.)

Primary Examiner—Weilun Lo
Assistant Examiner—Jamisue A. Webb
(74) Attorney, Agent, or Firm—Alyssa A. Dudkowski

(57) ABSTRACT

The present invention relates to absorbent articles including skin care compositions. The skin care compositions of the invention are stable on the bodyside liners of absorbent articles despite not containing an immobilizing agent. Surprisingly, the skin care compositions of the invention even demonstrate less migration away from the bodyside liner than do other compositions that contain so-called "immobilizing agents". The compositions of the invention possess physical properties, such as melting points, viscosities and hardnesses, comparable to compositions containing immobilizing agents, making them suitable for use on absorbent articles.

10 Claims, 5 Drawing Sheets

U.S. PATENT DOCUMENTS

| | | | |
|---|---|---|---|
| 4,634,438 A | 1/1987 | Sustmann et al. | |
| 4,634,439 A | 1/1987 | Sustmann et al. | |
| 4,637,820 A | 1/1987 | Marini et al. | |
| 4,655,756 A | 4/1987 | Fawkes | |
| 4,657,537 A | 4/1987 | Zimmerer | |
| 4,675,014 A | 6/1987 | Sustmann et al. | |
| 4,685,909 A | 8/1987 | Berg et al. | |
| 4,711,780 A | 12/1987 | Fahim | |
| 4,732,797 A | 3/1988 | Johnson et al. | |
| 4,738,678 A | 4/1988 | Paulis | |
| 4,753,643 A | 6/1988 | Kassai | |
| 4,753,647 A | 6/1988 | Curtis | |
| 4,760,096 A | 7/1988 | Sakai et al. | |
| 4,772,501 A | 9/1988 | Johnson et al. | |
| 4,790,836 A | 12/1988 | Brecher | |
| 4,790,840 A | 12/1988 | Cortina | |
| 4,798,603 A | 1/1989 | Meyer et al. | |
| 4,808,175 A | 2/1989 | Hansen | |
| 4,834,737 A | 5/1989 | Khan | |
| 4,861,405 A | 8/1989 | Kassai | |
| 4,882,204 A | 11/1989 | Tenenbaum | |
| 4,911,932 A | 3/1990 | Clum et al. | |
| 4,931,052 A | 6/1990 | Feldman | |
| 4,960,592 A | 10/1990 | Hagen et al. | |
| 4,978,534 A | 12/1990 | Saitoh | |
| 4,990,144 A | 2/1991 | Blott | |
| 4,996,238 A | 2/1991 | Matravers | |
| 5,043,155 A | 8/1991 | Puchalski et al. | |
| 5,049,440 A | 9/1991 | Bornhoeft, III et al. | |
| 5,091,193 A | 2/1992 | Enjolras et al. | |
| 5,110,593 A | 5/1992 | Benford | |
| 5,139,790 A | 8/1992 | Snipes | |
| 5,141,803 A | 8/1992 | Pregozen | |
| 5,147,576 A | 9/1992 | Montague et al. | |
| 5,176,668 A | 1/1993 | Bernardin | |
| 5,176,672 A | 1/1993 | Bruemmer et al. | |
| 5,192,277 A | 3/1993 | Chung et al. | |
| 5,192,606 A | 3/1993 | Proxmire et al. | |
| 5,194,261 A | 3/1993 | Pichierri | |
| 5,232,691 A | 8/1993 | Lemole | |
| 5,244,668 A | 9/1993 | Snipes | |
| 5,306,486 A | 4/1994 | McCook et al. | |
| 5,336,212 A | 8/1994 | De Francesco | |
| 5,336,692 A | 8/1994 | Gans et al. | |
| 5,350,624 A | 9/1994 | Georger et al. | |
| 5,362,488 A | 11/1994 | Sibley et al. | |
| 5,364,382 A | 11/1994 | Latimer et al. | |
| 5,376,655 A | 12/1994 | Imaki et al. | |
| 5,384,125 A | 1/1995 | DiPippo et al. | |
| 5,409,903 A | 4/1995 | Polak et al. | |
| 5,436,007 A | 7/1995 | Hartung et al. | |
| 5,466,232 A | 11/1995 | Cadieux et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,525,346 A | 6/1996 | Hartung et al. | |
| 5,533,990 A | 7/1996 | Yeo | |
| 5,569,230 A | 10/1996 | Fisher et al. | |
| 5,578,310 A | 11/1996 | M'Timkulu et al. | |
| 5,601,871 A | 2/1997 | Krzysik et al. | |
| 5,605,749 A | 2/1997 | Pike et al. | |
| 5,607,760 A | 3/1997 | Roe | |
| 5,607,980 A | 3/1997 | McAtee et al. | |
| 5,609,587 A | 3/1997 | Roe | |
| 5,614,293 A | 3/1997 | Krzysik et al. | |
| 5,618,529 A | 4/1997 | Pichierri | |
| 5,618,850 A | 4/1997 | Coury et al. | |
| 5,631,012 A | 5/1997 | Shanni | |
| 5,635,191 A | 6/1997 | Roe et al. | |
| 5,643,588 A | 7/1997 | Roe et al. | |
| 5,643,899 A | 7/1997 | Elias et al. | |
| 5,648,083 A | 7/1997 | Blieszner et al. | |
| 5,650,218 A | 7/1997 | Krzysik et al. | |
| 5,652,049 A | 7/1997 | Suzuki | |
| 5,652,194 A | 7/1997 | Dyer et al. | |
| 5,658,559 A | 8/1997 | Smith | |
| 5,665,368 A | 9/1997 | Lentini et al. | |
| 5,693,037 A | 12/1997 | Lee et al. | |
| 5,695,868 A | 12/1997 | McCormack | |
| 5,738,859 A | 4/1998 | Posner | |
| H1732 H | 6/1998 | Johnson | |
| 5,801,107 A | 9/1998 | Everhart et al. | |
| 5,830,487 A | 11/1998 | Klofta et al. | |
| 5,843,056 A | 12/1998 | Good et al. | |
| 5,849,314 A | 12/1998 | Dobkowski et al. | |
| 5,855,897 A | 1/1999 | Pelle | |
| 5,855,999 A | 1/1999 | McCormack | |
| 5,856,245 A | 1/1999 | Caldwell et al. | |
| 5,869,033 A | 2/1999 | Schulz | |
| 5,869,075 A | 2/1999 | Krzysik | |
| 5,869,172 A | 2/1999 | Caldwell | |
| 5,871,763 A | 2/1999 | Luu et al. | |
| 5,879,341 A | 3/1999 | Odorzynski et al. | |
| 5,891,126 A | 4/1999 | Osborn, III et al. | |
| 5,938,649 A | 8/1999 | Ducker et al. | |
| 5,944,705 A | 8/1999 | Ducker et al. | |
| 5,945,110 A | 8/1999 | Vianen et al. | |
| 5,951,990 A | 9/1999 | Ptchelintsev | |
| 5,989,577 A | 11/1999 | Hoath et al. | |
| 5,990,377 A | 11/1999 | Chen et al. | |
| 6,004,566 A | 12/1999 | Friedman et al. | |
| 6,031,147 A | 2/2000 | Gross | |
| 6,051,749 A | 4/2000 | Schulz | |
| 6,075,179 A | 6/2000 | McCormack et al. | |
| 6,093,869 A | 7/2000 | Roe et al. | |
| 6,100,442 A | 8/2000 | Samuelsson et al. | |
| 6,103,245 A | 8/2000 | Clark et al. | |
| 6,107,537 A | 8/2000 | Elder et al. | |
| 6,117,439 A | 9/2000 | Kake | |
| 6,118,041 A | 9/2000 | Roe et al. | |
| 6,120,488 A | 9/2000 | VanRijswijck et al. | |
| 6,136,332 A | 10/2000 | Grollier et al. | |
| 6,149,934 A * | 11/2000 | Krzysik et al. | 424/443 |
| 6,152,906 A | 11/2000 | Faulks et al. | |
| 6,153,209 A | 11/2000 | Vega et al. | |
| 6,156,024 A | 12/2000 | Schulte et al. | |
| 6,166,285 A | 12/2000 | Schulte et al. | |
| 6,183,766 B1 | 2/2001 | Sine et al. | |
| 6,217,890 B1 | 4/2001 | Paul et al. | |
| 6,238,682 B1 | 5/2001 | Klofta et al. | |
| 6,287,581 B1 | 9/2001 | Krzysik et al. | |
| 6,294,186 B1 * | 9/2001 | Beerse et al. | 424/405 |
| 6,309,736 B1 | 10/2001 | McCormack et al. | |
| 6,316,030 B1 | 11/2001 | Kropf et al. | |
| 6,344,218 B1 | 2/2002 | Dodd et al. | |
| 2001/0006666 A1 | 7/2001 | Harbeck | |

FOREIGN PATENT DOCUMENTS

| | | |
|---|---|---|
| EP | 0 212 870 B1 | 4/1992 |
| EP | 0 613 675 A1 | 9/1994 |
| EP | 0 732 108 A2 | 9/1996 |
| EP | 0 797 968 A1 | 10/1997 |
| EP | 0 808 151 B1 | 11/1997 |
| EP | 0 815 841 A1 | 1/1998 |
| EP | 0 875 233 A1 | 11/1998 |
| EP | 0 922 452 A1 | 6/1999 |
| EP | 0 922 456 A1 | 6/1999 |
| EP | 1 057 476 A1 | 12/2000 |
| GB | 880276 | 10/1961 |

| GB | 884688 | 12/1961 |
| --- | --- | --- |
| GB | 2 033 751 A | 5/1980 |
| GB | 2 311 727 A | 10/1997 |
| WO | WO 90/12555 A1 | 11/1990 |
| WO | WO 92/09289 A1 | 6/1992 |
| WO | WO 93/16670 A1 | 9/1993 |
| WO | WO 93/21878 A1 | 11/1993 |
| WO | WO 94/09727 A1 | 5/1994 |
| WO | WO 94/09796 A1 | 5/1994 |
| WO | WO 95/19190 A1 | 7/1995 |
| WO | WO 96/16681 A1 | 6/1996 |
| WO | WO 96/16682 A1 | 6/1996 |
| WO | WO 97/05908 A2 | 2/1997 |
| WO | WO 97/05909 A2 | 2/1997 |
| WO | WO 97/38735 A1 | 10/1997 |
| WO | WO 97/38738 A1 | 10/1997 |
| WO | WO 98/03147 A1 | 1/1998 |
| WO | WO 98/47546 A1 | 10/1998 |
| WO | WO 98/55159 A2 | 12/1998 |
| WO | WO 99/12530 A1 | 3/1999 |
| WO | WO 99/13861 A1 | 3/1999 |
| WO | WO 99/26610 A1 | 6/1999 |
| WO | WO 99/26618 A1 | 6/1999 |
| WO | WO 99/26619 A1 | 6/1999 |
| WO | WO 99/45771 A1 | 9/1999 |
| WO | WO 99/45973 A1 | 9/1999 |
| WO | WO 99/45974 A1 | 9/1999 |
| WO | WO 99/45976 A1 | 9/1999 |
| WO | WO 99/46316 A2 | 9/1999 |
| WO | WO 00/38747 A2 | 7/2000 |
| WO | WO 00/64407 A1 | 11/2000 |
| WO | WO 00/64501 A1 | 11/2000 |
| WO | WO 00/64503 A1 | 11/2000 |
| WO | WO 00/69481 A1 | 11/2000 |
| WO | WO 00/69482 A1 | 11/2000 |
| WO | WO 00/69483 A1 | 11/2000 |
| WO | WO 00/69484 A1 | 11/2000 |

OTHER PUBLICATIONS

Patent Abstracts of Japan 02053709 A: Description of Masaru et al. , "Thixotropic Semi–Solid Composition."

Patent Abstracts of Japan 06065104 A: Description of Michio, "Powder Composition For Dermatic Application Prevented From Scatterability."

Patent Abstracts of Japan 07267839 A: Description of Yoshiko et al. , "Ointment Composition Adhesive to Oral Mucosa."

Patent Abstracts of Japan 09151112 A: Description of Yasuhiro et al. , "Microemulsion Composition."

Patent Abstracts of Japan 10037070 A: Description of Takeo, "Antimicrobial Fiber Containing Catechin of Green Tea Component."

Patent Abstracts of Japan 10306039 A: Description of Christine et al. , "Solid Topical Aqueous Composition Capable of Forming Film, When Applied, and Having Gel Appearance."

Patent Abstracts of Japan 55025430 A: Description of Mikio et al. , "Thickening and Gelling Agent."

Patent Abstracts of Japan 56110611 A: Description of Mitsue et al. , "Preparation of Ointment Embrocation For Skin."

Patent Abstracts of Japan 59053409 A: Description of Susumu et al. , "Base Composition and Pharmaceutical Composition for External Use."

Patent Abstracts of Japan 59122420 A: Description of Katsuo et al. , "Local Ointment."

Patent Abstracts of Japan 59227816 A: Description of Kenji et al. , "Skin Cleaning and Wiping Agent Composition."

Patent Abstracts of Japan 600006759 A: Description of Tadashi et al. , "Water–Dispersible Resin for Cataplasm."

Patent Abstracts of Japan 61129117 A: Description of Sakahito et al. , "Aloe–Containing Cataplasm."

Patent Abstracts of Japan 61194014 A: Description of Hiroshi et al. , "Hydrophilic Base."

Patent Abstracts of Japan 63264413 A: Description of Kazuo, "Gabexate Mesylate Ointment."

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: D 3236–88, "Standard Test Method for Apparent Viscosity of Holt Melt Adhesives and Coating Materials," pp. 326–331, published Dec. 1988.

Federal Test Method Standard (FTMS) No. 191A, Method 5514, "Water Resistance of Cloth; Low Range, Hydrostatic Pressure Method," Jul. 20, 1978, 3 pages.

Federal Test Method Standard (FTMS) No. 191A, Method 5450, "Permeability To Air; Cloth; Calibrated Orifice Method," Jul. 20, 1978, 5 pages.

Akin, Frank J. et al., "A Refined Method to Evaluate Diapers for Effectiveness in Reducing Skin Hydration Using the Adult Forearm," *Skin Research and Technology*, 1997, pp. 173–176.

Barbero, G.J. et al., Stool Trypsin and Chymotrypsin, *American Journal of Diseases of Children*, vol. 112, Jul. through Dec., 1966, pp. 536–540.

Barry, B.W. and A.J. Grace, "Investigation of Semisolid Lipophilic Preparations by Small Strain and Continuous Shear Viscometry and Their Application to Texture Profile," *Journal of Pharmaceutical Sciences*, vol. 60, No. 6, Jun. 1971, pp. 814–820.

Berg, Ronald W. et al., "Association of Skin Wetness and pH With Diaper Dermatitis," *Pediatric Dermatology*, vol. 11, No. 1, Mar. 1994, pp. 18–20.

Boylan, James C., "Rheological Study of Selected Pharmaceutical Semisolids," *Journal of Pharmaceutical Sciences*, vol. 55, No. 7, Jul. 1996, pp. 710–715.

Braudo, E.E. et al., "The Effect Produced by the Green Tea Components and Tannin on the Fermentative Activity of Trypsin in Vitro," Vopr Pitan, vol. 27, Issue No. 6, Nov.,Dec. 1968, pp. 40–44. (Russian w/English summary).

Bremecker, K.D. et al., "Novel Concept for a Mucosal Adhesive Ointment," *Journal of Pharmaceutical Sciences*, vol. 73, No. 4, Apr. 1984, pp. 548–552.

Davies, Owen L. and Peter L. Goldsmith, editors, *Statistical Methods in Research and Production*, Fourth Revised Edition, published by Longman Inc., New York, 1984, p. 460.

Davis, S.S. et al., "Some Limitations of Continous Shear Methods for the Study of Pharmaceutical Semi–Solids," *Journal of Pharmacy and Pharmacology*, vol. 20, Supplemental Issue, Dec. 1968, pp. 157S–167S.

Drechsler, Lee Ellen et al., "The Wipe: A Carrier of Skin Benefits," *Cosmetics & Toiletries*, vol. 116, No. 10, Oct. 2001, pp. 33–36, 38, 40, 42.

Eccleston, G.M. et al., "Correlation of Viscoelastic Functions for Pharmaceutical Semisolids: Comparison of Creep and Oscillatory Tests for Oil–in–Water Ceams Stabilized by Mixed Emulsifiers," *Journal of Pharmaceutical Sciences*, vol. 62, No. 12, Dec. 1973, 1954–1961.

Eccleston, G.M., "Structure and Rheology of Cetomacrogol Creams: The Influence of Alcohol Chain Length and Homologue Composition," *Journal of Pharmacy and Pharmacology*, vol. 29, No. 3, Mar. 1977, pp. 157–162.

Eros, I. and A. Thaleb, "Rheological Studies of Creams: I. Rheological Functions and Structure of Creams," *Acta Pharmaceutica Hungarica*, vol. 64, No. 3, May 1994, pp. 101–103.

Fuhrer, C., "Gel Structure of Fatty Alcohols in Ointment Bases," *Pharmazie*, vol. 26, No. 1, Jan. 1971, pp. 43–45 (German).

Haverback, Bernard J. et al., "Measurement of Trypsin and Chymotrypsin in Stool: A Diagnostic Test for Pancreatic Exocrine Insuffieciency," *Gastroenterology*, vol. 44, 1963, pp. 588–597.

Huttenrauch, R., "Activation Energies in Plastic Deformation of Ointment Gels," *Pharmazie*, vol. 28, No. 4, Apr. 1973, 244–249. (German).

Imai, Satoshi and Chihiro Kuwabara, "Infant Skin and Its Care," *Cosmetics & Toiletries*, vol. 107, Jul. 1992, pp. 85–86, 88–90.

Kedzierewicz, F. et al., "Preparation of Silicone Microspheres by Emulsion Polymerization: Application to the Encapsulation of a Hydrophilic Drug," *Journal of Microencapsulation*, vol. 15, No. 2, Mar.–Apr. 1998, pp. 227–236.

Muguet, V. et al., "Formation of Shear Rate Sensitive Multiple Emulsions," *Journal of Controlled Release*, vol. 70, No. 1–2, Jan. 29, 2001, pp. 37–49.

Odio, Mauricio R. et al., "Continuous Topical Administration of a Petrolatum Formulation by a Novel Disposable Diaper. 1. Effect on Skin Surface Microtopography," *Dermatology*, 2000; 200(3):232–237.

Odio, Maurico R. et al., "Continuous Topical Administration of a Petrolatum Formulation by a Novel Disposable Diaper. 2. Effect on Skin Condition," *Dermatology*, 2000; 200(3):238–243.

Pena, Lorraine E. et al., "Structural Rheology of a Model Ointment," *Pharmaceutical Research, vol. 11, No. 6*, Jun. 1994, pp. 875–881.

Popovici, Iuliana et al., "The Physico–Chemical Characterization and Therapeutic Evaluation of Cicatrol," *Revista Medico–Chirurgicala Societatii Medici si Naturalisti din Lasi*, vol. 96, No. 1–2, Jan.–Jun. 1992, pp. 57–64.

Preston, Sandra L. et al., "Etiology and Treatment of Diaper Dermatitis," *Hospital Pharmacy*, vol. 29, No. 12, Dec. 1994, pp. 1086–1088, 1097.

Salo, D.P. et al., "Ion Exchange Properties of Clay Minerals and Its Use for Obtaining Clays With Planned Properties. 3. Effect of the Nature of Exchange Kation on the Structure-Mechanical Properties of Suspensions and Ointment Bases Prepared From Clays of Montmorillonite and Sepiolite-Mountain Leather Groups," *Farm Zh*, vol. 23, No. 6, 1968, pp. 61–66. (Ukrainian).

Sires, Ulrike I. and Susan B. Mallory, "Diaper Dermatitis—How to Teant and Prevent," *Postgraduate Medicine*, vol. 98, No. 6, Dec. 1995, pp. 79–82, 84, 86.

Taleb, A. and I. Eros, "Rheological Studies of Creams. II Effect of Water Content on Rheological Characteristics," *Acta Pharmaceutica Hungarica*, vol. 66, No. 2, Mar. 1996, pp. 71–76.

Tamburic, S. et al., "An Investigation Into the Use of Thermorheology and Texture Analysis in the Evaluation of W/O Creams Stabilized With a Silicone Emulsifier," *Pharmaceutical Development Technology*, vol. 1, No. 3, Oct. 1996, pp. 299–306.

Vinson, Joe an John Proch, "Inhibition of Moisture Penetration to the Skin by a Novel Incontinence Barrier Product," *Journal of Wound Ostomy Continence Nursing*, vol. 25, No. 5, Sep. 1998, pp. 256–260.

Zielinski, Ruth and Elizabeth Hanson, "Diaper Dermatitis: Medical Aspects of Skin Care," *Nonwovens World*, Feb.–Mar. 2000, pp. 60–65.

* cited by examiner

ABSORBENT ARTICLES WITH SIMPLIFIED COMPOSITIONS HAVING GOOD STABILITY

The present application is being filed as a continuation-in-part and therefore, claims priority to the filing date of U.S. patent application Ser. No. 09/746,880 filed on Dec. 22, 2000 and entitled "Absorbent Articles with Non-Aqueous Compositions Containing Anionic Polymers".

BACKGROUND OF THE INVENTION

The present invention relates to the use of compositions that are stable on the body-facing materials of disposable absorbent articles, such as diapers, training pants, adult incontinence products, underpants, feminine care products, nursing pads, wound dressings and similar articles having absorbent capacity. Unexpectedly, the compositions are stable despite not including immobilizing agents previously believed necessary for stability on the body-facing materials. Consequently, the compositions are also simplified, i.e. contain fewer ingredients, from previously known compositions. The viscosity, hardness and overall stability of the simplified compositions were unexpected based on previously taken approaches to delivering a composition from a body-facing material of an absorbent article.

Absorbent articles such as diapers, training pants, incontinence products and feminine care products are worn such that they are in direct contact with the skin of the wearer. An unavoidable consequence of the use of absorbent articles is that the skin is exposed more directly to various physical and biological insults. Consequently, the barrier function of the skin covered by the absorbent article is put at risk. In order to provide disposability, absorbent articles are primarily constructed of nonwoven materials. Even though nonwoven materials are engineered to have soft hand and drape, they rub against the skin and there is friction. Such friction constitutes one form of physical insult to the skin barrier. Friction against the skin barrier also occurs with the use of absorbent tissues and wipes. Absorbent tissue and wipe products are frequently used for cleansing the skin areas covered by absorbent articles. Absorbent tissue and wipe products are necessary for removing biological waste materials from the skin.

In addition to these physical insults, skin covered by absorbent articles is also frequently exposed to biological insults. Biological fluids, such as urine, feces, vaginal secretions and nasal secretions, may contain a variety of components that can damage the skin barrier. Examples of these components include proteases, lipases and bile acids. Once the skin barrier is compromised, these components, in addition to other constituents of biological fluids, can initiate or exacerbate inflammation of the skin. As a result of the physical and chemical insults that skin covered by absorbent articles must endure, substantial work has been done to deliver compositions to the skin from the absorbent articles. Desirably, the compositions preserve the skin's own barrier function. However, the compositions can also repair or restore barrier function to skin that has been damaged.

Disposable absorbent articles such as diapers, training pants, adult incontinence products, underpants, feminine care products and nursing pads have been used to absorb body fluids and leave the skin dry. Disposable absorbent articles of this type generally include a liquid impermeable backsheet member, an absorbent core or assembly, and a liquid permeable body facing or liner material. The body facing or liner material comes into contact with the wearer's skin. While the body facing material is made of a soft, compliant material, the material rubs against the skin during use and may not leave the skin completely dry and free of the bodily fluids, such as solid or semi-solid waste, the absorbent article is trying to absorb. During frequent insults of bodily fluids and frequent use of disposable absorbent articles, the skin can become irritated and appear red and be sore to the touch.

Substantial efforts have been made to provide skin care compositions on the bodyfacing surfaces of disposable absorbent articles. The efforts have focused on providing skin care compositions on the bodyside liners of such articles because the bodyside liner typically has the greatest surface area coming into contact with the skin of the wearer of the article. Frequently, the benefits perceived to be obtained from the skin care compositions are only realized if the skin care composition is transferred to the skin of the wearer of the article. Hence, the desire to apply the compositions to the portion of the article having the greatest area of contact with the skin. It is also known to provide skin care compositions on the containment flaps, leg elastics, waist elastics and other portions of absorbent articles that come into direct contact with the wearer's skin.

Application of skin care compositions to absorbent articles has been known since the early 1970s. In the 1990s, efforts shifted to describing compositions that would remain where they were originally applied and that would not migrate to other portions of the article. U.S. Pat. No. 5,643,588 (issued on Jul. 1, 1997 to Roe et al.) describes a disposable diaper having a lotion coating on the topsheet of the diaper. The lotion coating is described as including an emollient and an immobilizing agent; the immobilizing agent prevents the flow or migration of the emollient into the diaper. The emollient is described as including petroleum-based, fatty acid ester type, alkyl ethoxylate type, fatty acid ester ethoxylates, fatty alcohol type, polysiloxane type or mixtures of such emollients. Suitable immobilizing agents are described as including $C_{14}$–$C_{22}$ fatty alcohols, $C_{12}$–$C_{22}$ fatty acids, $C_{12}$–$C_{22}$ fatty alcohol ethoxylates having an average degree of ethoxylation ranging from 2 to about 30, waxes and mixtures of such ingredients.

The Roe patent describes the emollient in the lotion coating as having a plastic or fluid consistency at 20 deg. C. and as tending to flow or migrate into the interior of the diaper. Roe et al. describe that this migration of the emollient into the interior of the diaper can cause undesired effects on the absorbency of the diaper core due to the hydrophobic characteristics of many of the emollients. Roe et al also recognize that migration of the emollient in the lotion coating means that much more emollient has to be applied to the diaper topsheet. Increasing the quantity of emollient that must be applied not only increases the cost, but also exacerbates the undesirable effect on the absorbency of the diaper core. Roe et al. go on to recognize that the immobilizing agent counteracts this tendency of the emollient to migrate or flow by keeping the emollient primarily localized on the surface of the diaper topsheet.

Separate efforts have been made to identify compounds—distinct from those that could be considered "emollients" or "immobilizing agents"—capable of reducing lotion migration. U.S. Pat. No. 6,149,934 (issued to Krzysik et al. on Nov. 21, 2000) describes an absorbent article having a lotion formulation on the bodyside liner of the article where the lotion formulation includes an emollient, a wax and a viscosity enhancer. Krzysik et al. describe the viscosity enhancer component as helping to stabilize the formulation on the bodyfacing surface of the bodyside liner in order to reduce migration and to improve transfer to the skin.

Krzysik et al. describe suitable viscosity enhancers as including polyolefin resins, lipophilic/oil thickeners, ethylene/vinyl acetate copolymers, polyethylene, silica, talc, colloidal silicone dioxide, zinc stearate, cetyl hydroxy ethyl cellulose, other modified celluloses and mixtures of such compounds.

The need for compositions that remain on and do not migrate away from the liner (and other bodyfacing surfaces) of absorbent articles has been well recognized. However, as work in the area of composition formulation continues, the compositions tend to increase in their complexity (for example, the number of ingredients). For a number of reasons, it would be beneficial to reduce the number of ingredients used in skin care compositions formulated for application to absorbent articles. Benefits include better quantification of individual ingredients in the blend, reduced handling and processing of individual ingredients and reduced cost associated with elimination of ingredients. Therefore, there remains a need for a skin care composition for application to the bodyfacing surfaces of absorbent articles having a simplified formula but still delivering the performance need of stability on the surfaces to which it is applied.

SUMMARY OF THE INVENTION

In response to the difficulties and problems discussed above, compositions having simplified formulations and good stability (despite not containing an immobilizing agent) have been discovered. While the compositions of the inventions can have a variety of applications, the compositions are particularly beneficial when used in conjunction with absorbent articles such as diapers, incontinence garments, feminine care products, training pants, diaper pants, nursing pads and wound dressings. A further benefit of the compositions of the invention is that the compositions have viscosities and penetration hardnesses comparable to compositions that include immobilizing agents. The purposes and advantages of the present invention will be set forth in and apparent from the description that follows, as well as will be learned by practice of the invention. Additional advantages of the invention will be realized and attained by the compositions and articles particularly pointed out in the written description and claims hereof, as well as from the appended drawings.

In one aspect, the present invention relates to an absorbent article that includes an outer cover, a bodyside liner, an absorbent body and a composition. The bodyside liner is typically liquid permeable and defines a bodyfacing surface. The bodyside liner is connected in a generally superposed relation to the outer cover. The absorbent body is located between the bodyside liner and the outer cover. The composition is on a portion or the entire bodyfacing surface of the bodyside liner. The composition can be generally solid, semi-solid or liquid. The composition may be in a variety of forms, including, but not limited to, emulsions, lotions, creams, ointments, salves, suspensions, gels and the like. The composition can be applied to the bodyside liner using a variety of techniques including foam application, spraying, slot coating and printing. The present invention also encompasses technology that would permit integration of the composition directly with fibers or other materials used to form the bodyside liner. The compositions can be applied to the bodyfacing surface in amounts of from about 0.1 grams per meter squared ($g/m^2$) to about 30 $g/m^2$. The compositions of the invention could also be applied to or be present on other skin contacting surfaces of absorbent articles such as the waist and leg elastics and the containment flaps.

The compositions of the invention can include from about 40 to about 99 percent by weight of one or more emollients. More specifically, the compositions include from about 60 to about 95 percent by weight of emollient(s). Emollients are skin conditioning ingredients that help to soften, smooth, plasticize, lubricate, moisturize, improve the appearance of, improve the feel of and protect the skin. Even more specifically, the compositions include from about 75 to about 90 percent by weight of emollient(s). Suitable emollients include petrolatum; partially hydrogenated vegetable and animal oils; fatty acid esters having a melting point greater than 30° C.; alkyl silicones having a melting point greater than 30° C.; lanolin; triglycerides having a melting point greater than 30° C. and mixtures thereof.

The compositions of the invention can also include from about 1 to about 60 percent by weight of one or more compounds acting as stability enhancers that increase the meltpoint viscosity of the emollients of the composition. More specifically, the compositions include from about 5 to about 40 percent by weight of one or more stability enhancers. Even more specifically, the compositions include from about 10 to about 25 percent by weight of stability enhancer (s).

Examples of suitable stability enhancers include polyolefin resins, ethylene/vinyl acetate copolymers, polyethylene, silica, silica silylate, silica methyl silylate, alkyl hydroxy ethyl cellulose, quaternary starch compounds, natural clays, synthetic analogs of natural clays, organically modified clays, quaternary modified clays, colloidal silicone dioxide, magnesium aluminum silicate, polymethacrylate polymers, polystyrene copolymers and mixtures thereof.

The compositions of the invention do not include compounds that are understood to act as immobilizing agents for the emollients. Until now, it was believed that in order to prevent the migration of the emollient(s) away from the bodyside liner of the article it was necessary to include an immobilizing agent in the composition. Compounds that have been recognized as immobilizing agents include $C_{14}$–$C_{22}$ fatty alcohols, $C_{12}$–$C_{22}$ fatty acids, $C_{12}$–$C_{22}$ fatty alcohol ethoxylates having an average degree of ethoxylation ranging from 2 to about 30 and waxes. It is believed that the immobilizing agents stabilized the emollients by increasing the melting point of the compositions in which they were included. The increase in melting point led to an increased viscosity at a given temperature. It is believed that the stability enhancers of the invention can perform the function previously performed by the immobilizing agents by contributing to the viscosity of the composition (as opposed to increasing the melting point). Unexpectedly, the compositions of the invention have physical properties similar to conventional compositions containing immobilizing agents.

The compositions of the invention can also include from about 0.1 to about 59 percent by weight of natural fats or natural oils. More specifically, the compositions can include from about 5 to about 45 percent by weight of natural fats or natural oils. Desirably, the compositions of the invention include from about 10 to about 30 percent by weight of natural fats, natural oils or mixtures of both. Natural fats and oils include fats, oils, essential oils, fatty acids, fatty alcohols, phospholipids and mixtures of these compounds. The natural fats and oils can be similar to the lipids that are present in healthy skin in order to mimic the naturally present lipids. Synthetic or synthetically modified fats and oils could potentially also be used if they functioned in the same manner as their natural counterparts.

The compositions can also include sterols, sterol derivatives or mixtures of both in an amount of from about 0.1 to about 10 percent by weight. Sterols and sterol derivatives include compounds such as β-sterols with a tail on the 17 position and no polar groups, such as cholesterol, $C_{10}$–$C_{30}$ cholesterol/lanosterol esters, tall oil sterols, soy sterols, sterol esters and mixtures of these compounds. More specifically, the compositions include from about 0.5 to about 5 percent by weight of sterols, sterol derivatives or mixtures of both. Even more specifically, the compositions include from about 0.8 to about 1 percent by weight of the sterol compounds.

In addition to the components already described, the compositions of the invention may also include active ingredients such as those ingredients that may be useful for treating skin irritations such as diaper rash. Examples of such active ingredients include allantoin and its derivatives, aloe, aluminum hydroxide gel, calamine, cocoa butter, cod liver oil, dimethicone, glycerin, kaolin and its derivatives, lanolin and its derivatives, mineral oil, petrolatum, white petrolatum, shark liver oil, talc, topical starch, zinc acetate, zinc carbonate, zinc oxide and mixtures of these ingredients. Some of the ingredients listed as possible active ingredients for treating the skin can also be used as emollients.

Ranges are used to describe the relative quantities of compounds in the compositions of the invention and ranges are used to describe the relative physical properties of the compositions of the invention. It is understood that the ranges are by way of illustration only and that one of skill in the art would recognize that the nature of the specific compositions dictates the levels to be applied to achieve the desired results. The levels of components are ascertainable by routine experimentation in view of the present disclosure.

The compositions of the invention typically have a melting point of from about 32° C. to about 100° C. Melting behavior in this range provides compositions that are relatively immobile and localized on the bodyfacing surface of the bodyside liner of the absorbent article at room temperature. Though relatively immobile and localized at room temperature, the compositions are also readily transferable to the wearer of the article at body temperature through natural rubbing or friction during wearing and through adhesion of the composition to the skin of the wearer. The compositions also maintain their integrity and are not completely liquid at elevated temperatures such as may be experienced during storage. Stability in a solid state at elevated temperatures is made possible, in part, by the increase in viscosity provided by the stability enhancers. Desirably, the compositions of the invention are easily transferable to the skin by way of normal contact, including adhesion of the composition to the skin, wearer motion or body heat. Because the compositions are relatively stable on the bodyfacing surfaces of the articles, the quantities of the compositions necessary to provide the desired skin barrier benefits are reduced. In addition, special barrier or wrapping materials may not be necessary for the articles of the invention.

The compositions of the invention have high shear viscosities of greater than about 40 centipoise at processing temperatures such as at a temperature of about 60° C. or higher. The melting points and, therefore, the processing temperatures vary for different compositions of the invention. The compositions may also have a penetration hardness of from about 2 millimeters to about 100 millimeters at 25° C.

In another aspect, the compositions of the invention demonstrate improved stability on the bodyside liners of the absorbent articles. More specifically, when the compositions of the invention contain about 10% or more of stability enhancer(s), the compositions exhibit less than 10% loss from a bodyside liner material. Further, when the compositions of the invention contain about 10% by weight or less of stability enhancer(s), the compositions exhibit less than about 20% loss from a bodyside liner material.

The absorbent articles and compositions of the invention advantageously deliver the benefits of conventional skin care compositions provided on absorbent articles but with simplified formulations. The skin care compositions of the invention provide a vehicle for delivering emollients that soothe and protect the skin without the need for an immobilizing agent. Further, by not needing an immobilizing agent, the skin care compositions of the invention have more formulation flexibility; for example, greater quantities of skin care active ingredients could be used to provide more efficacious compositions. It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles and compositions of the invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the claims. Like parts of the absorbent articles depicted in the drawings are referred to by the same reference numerals.

DETAILED DESCRIPTION OF THE INVENTION

The present invention is directed to solving problems related to simplifying the formulations of compositions that are applied to the bodyfacing surfaces of absorbent articles. Similarly, the present invention is directed to solving problems related to eliminating the need for immobilizing agents in order to provide stability of the emollient component(s) of compositions applied to the bodyfacing surfaces of absorbent articles. Further, the present invention is related to providing skin care compositions on the bodyfacing surfaces of absorbent articles that experience less loss from those surfaces under storage and transportation conditions.

The present disclosure of the invention will be expressed in terms of its various components, elements, constructions, configurations, arrangements and other features that may also be individually or collectively referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components or groups thereof.

The present invention encompasses absorbent articles including simplified compositions that do not require components that were previously believed to be necessary for stability. The following detailed description will be made in the context of one type of absorbent article, a disposable diaper that is adapted to be worn by infants about their lower torso. It is readily apparent, however, that the absorbent article of the present invention would also be suitable for use as another type of absorbent article, such as a feminine care pad, interlabial device, an incontinence garment, a training pant, a prefastened or refastenable diaper pant, a wound dressing or a nursing pad.

Figure 1:
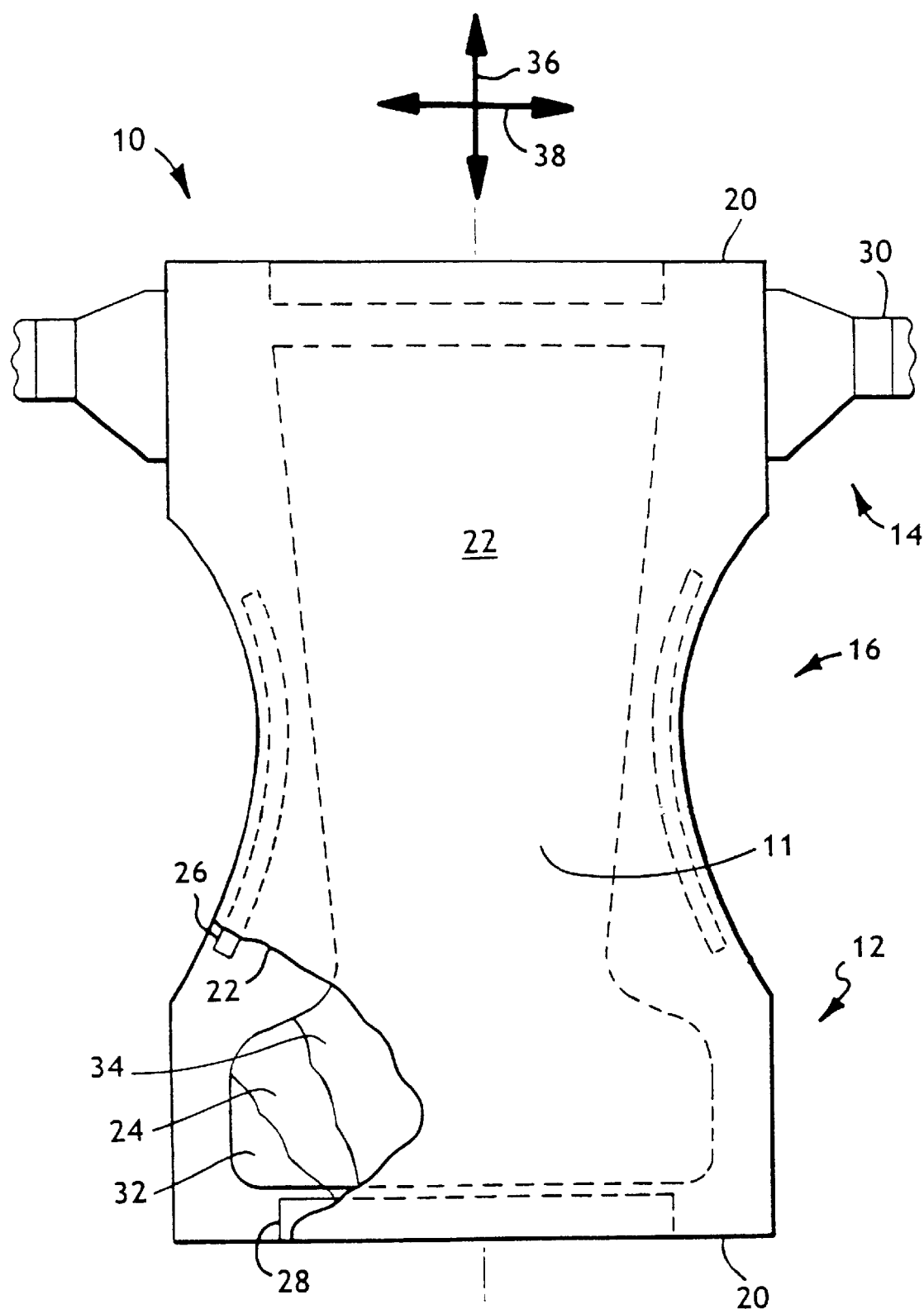
FIG. 1 representatively shows a partially cut away, top plan view of an absorbent article according to one aspect of the invention in a stretched and laid flat condition with the surface of the article that contacts the skin of the wearer facing the viewer.

FIG. 1 is a representative plan view of a disposable diaper 10 of the present invention in a flat-out, uncontracted state (i.e., with all elastic induced gathering and contraction removed). The bodyfacing surface 11 of the diaper 10, that is, the surface 11 of the diaper 10 that contacts the wearer is facing the viewer. The compositions of the invention can be applied to one or more bodyfacing materials that are components of the diaper 10. As used herein, the term 'bodyfacing material' includes, but is not limited to, materials such as the bodyside liner or topsheet, elastic material, tissue, intake and distribution material, absorbent material, and backsheet material. Each of these materials and components of a diaper 10 are described more fully herein. The compositions of the invention are applied to one or more of the bodyfacing materials in order to have maximum exposure and opportunity to transfer to the skin of the wearer of the diaper. The bodyfacing material of the present invention can be a single layer or multi-layered.

With reference to FIG. 1, the diaper 10 generally defines a front waist section 12, a rear waist section 14, and an intermediate section 16 that interconnects the front and rear waist sections 12 and 14. The front and rear waist sections 12 and 14 include the general portions of the diaper 10 that are constructed to extend substantially over the wearer's front and rear abdominal regions, respectively, during use. The intermediate section 16 of the diaper 10 includes the general portion of the diaper 10 that is constructed to extend through the wearer's crotch region between the legs.

The diaper 10 includes a vapor permeable backsheet or outer cover 20, a liquid permeable topsheet or bodyside liner 22 positioned in facing relation with the outer cover 20, and an absorbent body 24, such as an absorbent pad, which is located between the outer cover 20 and the bodyside liner 22. The outer cover 20 defines a length and a width that, in the illustrated aspect, coincide with the length and width of the diaper 10. The absorbent body 24 generally defines a length and width that are less than the length and width of the outer cover 20, respectively. Thus, marginal portions of the diaper 10, such as marginal sections of the outer cover 20, may extend past the terminal edges of the absorbent body 24. In the illustrated aspects, for example, the outer cover 20 extends outwardly beyond the terminal marginal edges of the absorbent body 24 to form side margins and end margins of the diaper 10. The bodyside liner 22 is generally coextensive with the outer cover 20 but may optionally cover an area that is larger or smaller than the area of the outer cover 20, as desired. In other words, the bodyside liner 22 is connected in superposed relation to the outer cover 20. The outer cover 20 and bodyside liner 22 are intended to face the garment and body of the wearer, respectively, while in use.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIG. 1, the diaper 10 may include leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. In the illustrated aspects, the elastic members are illustrated in their uncontracted, stretched condition for the purpose of clarity.

Fastening means, such as hook and loop fasteners 30, are employed to secure the diaper 10 on a wearer. Alternatively, other fastening means, such as buttons, pins, snaps, adhesive tape fasteners, cohesives, mushroom-and-loop fasteners, or the like, may be employed. Additionally, more than two fasteners can be provided, particularly if the diaper 10 is to be provided in a prefastened configuration. The fasteners can vary in size and form.

The diaper 10 may further include other layers between the absorbent body 24 and the bodyside liner 22 or outer cover 20. For example, as representatively illustrated in FIGS. 1 and 2, the diaper 10 may include a ventilation layer 32 located between the absorbent body 24 and the outer cover 20 to insulate the outer cover 20 from the absorbent body 24, to improve air circulation and to effectively reduce the dampness of the garment facing surface of the outer cover 20. The ventilation layer 32 may also assist in distributing fluid exudates to portions of the absorbent body 24 that do not directly receive the insult. The diaper 10 may also include a surge management layer 34 located between the bodyside liner 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hourglass shape. In the shown aspect, the diaper 10 has a generally I-shape. The diaper 10 further defines a longitudinal direction 36 and a lateral direction 38. Other suitable diaper components that may be incorporated on absorbent articles of the present invention include containment flaps, waist flaps, elastomeric side panels, and the like which are generally known to those skilled in the art. Likewise, if the diaper 10 is to be sold in a prefastened condition, the diaper 10 may have passive bonds (not shown) that join the rear waist section 14 with the front waist section 12.

Examples of diaper configurations suitable for use in connection with the instant application that may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; U.S. Pat. No. 5,496,298 issued Mar. 5, 1996 to Kuepper et al.; U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown aspect, for example, the bodyside liner 22 and outer cover 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper 10 by employing the above-identified attachment mechanisms.

The outer cover 20 of the diaper 10, as representatively illustrated in FIG. 1, is composed of a substantially vapor permeable material. The permeability of the outer cover 20 is configured to enhance the breathability of the diaper 10 and to reduce the hydration of the wearer's skin during use without allowing excessive condensation of vapor, such as urine, on the garment facing surface of the outer cover 20 that can undesirably dampen the wearer's clothes. The outer cover 20 is generally constructed to be permeable to at least water vapor and has a water vapor transmission rate of at least about 1000 $g/m^2/24$ hr., desirably at least about 1500 $g/m^2/24$ hr, more desirably at least about 2000 $g/m^2/24$ hr., and even more desirably at least about 3000 $g/m^2/24$ hr. For example, the outer cover 20 may define a water vapor transmission rate of from about 1000 to about 6000 $g/m^2/24$ hr. Materials that have a water vapor transmission rate less than those above do not allow a sufficient amount of air exchange and undesirably result in increased levels of skin hydration.

The outer cover 20 is also desirably substantially liquid impermeable. For example, the outer cover 20 may be constructed to provide a hydrohead value of at least about 60 cm, desirably at least about 80 cm, and more desirably at least about 100 cm when subjected to the Hydrostatic Pressure Test. Materials that have hydrohead values less than those above undesirably result in the strike through of liquids, such as urine, during use. Such fluid strike through can undesirably result in a damp, clammy feeling on the outer cover 20 during use. The methods by which Water Vapor Transmission Rate and Hydrostatic Pressure can be measured are described in U.S. Pat. No. 6,217,890 issued Apr. 17, 2001 to Paul et al. and incorporated herein by reference.

The outer cover 20 may be composed of any suitable materials that either directly provide the above desired levels of liquid impermeability and air permeability or, in the alternative, materials that can be modified or treated in some manner to provide such levels. In one aspect, the outer cover 20 may be a nonwoven fibrous web constructed to provide the required level of liquid impermeability. For example, a nonwoven web composed of spunbond or meltblown polymer fibers may be selectively treated with a water repellent coating or laminated with a liquid impermeable, vapor permeable polymer film to provide the outer cover 20. In a particular aspect of the invention, the outer cover 20 may include a nonwoven web composed of a plurality of randomly deposited hydrophobic thermoplastic meltblown fibers that are sufficiently bonded or otherwise connected to one another to provide a substantially vapor permeable and substantially liquid impermeable web. The outer cover 20 may also include a vapor permeable nonwoven layer that has been partially coated or otherwise configured to provide liquid impermeability in selected areas.

Examples of suitable materials for the outer cover 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. Pat. No. 6,309,736 issued Oct. 30, 2001, in the name of McCormack et al. and entitled "LOW GAUGE FILMS AND FILM/NONWOVEN LAMINATES", the disclosures of which are herein incorporated by reference.

In a particular aspect, the outer cover 20 is provided by a microporous film/nonwoven laminate material that includes a spunbond nonwoven material laminated to a microporous film. The spunbond nonwoven comprises filaments of about 1.8 denier extruded from a copolymer of ethylene with about 3.5 weight percent propylene and defines a basis weight of from about 17 to about 25 grams per square meter. The film includes a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight of from about 30 to about 60 grams per square meter and a water vapor transmission rate of from about 3000 to about 6000 $g/m^2/24$ hr. Examples of such film/nonwoven laminate materials are described in more detail in U.S. Pat. No. 6,309,736 issued Oct. 30, 2001, in the name of McCormack et al.

In another aspect, the outer cover 20 is provided by an extensible material. Further, the outer cover 20 can also be provided by a material having stretch in both the longitudinal 36 and lateral 38 directions. Extensible and stretchable outer cover materials can be used in absorbent articles to provide various benefits including better fitting articles.

The bodyside liner 22, as representatively illustrated in FIG. 1, defines a bodyfacing surface 11 that is compliant, soft feeling, and nonirritating to the wearer's skin. Further, the bodyside liner 22 may be less hydrophilic than the absorbent body 24, to present a relatively dry surface to the wearer, and may be sufficiently porous to be liquid permeable, permitting liquid to readily penetrate through its thickness. A suitable bodyside liner 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 22 is suitably employed to help isolate the wearer's skin from liquids held in the absorbent body 24.

Various woven and nonwoven fabrics can be used for the bodyside liner 22. For example, the bodyside liner 22 may be composed of a meltblown or spunbond web of polyolefin fibers. The bodyside liner 22 may also be a bonded-carded web composed of natural and/or synthetic fibers. The bodyside liner 22 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 22 includes a nonwoven, spunbond, polypropylene fabric composed of about 1.8–3.2 denier fibers formed into a web having a basis weight of about 22 grams per square meter and a density of about 0.06 gram per cubic centimeter.

In a particular aspect of the present invention, the bodyside liner 22 may be surface treated with about 0.3 weight percent of a surfactant mixture that contains a mixture of AHCOVEL Base N-62 and GLUCOPON 220UP surfactants in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation and includes alkyl polyglycoside. The surfactant may also include additional ingredients such as aloe. The surfactant may be applied by any conventional means, such as spraying, printing, brush coating, foam or the like. The surfactant may be applied to the entire bodyside liner 22 or may be selectively applied to particular sections of the bodyside liner 22, such as the medial section along the longitudinal centerline of the diaper, to provide greater wettability of such sections.

The absorbent body 24 of the diaper 10, as representatively illustrated in FIG. 1, may suitably comprise a matrix of hydrophilic fibers, such as a web of cellulosic fluff, mixed with particles of a high-absorbency material commonly known as superabsorbent material. In a particular aspect, the absorbent body 24 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent body 24 may include a laminate of fibrous webs and superabsorbent material or other suitable matrix for maintaining a superabsorbent material in a localized area.

The absorbent body 24 may have any of a number of shapes. For example, the absorbent body 24 may be rectangular, I-shaped, or T-shaped. It is generally preferred that the absorbent body 24 is narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated aspects, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied. In a particular aspect of the invention, the absorbent body 24 has an absorbent capacity of at least about 300 grams of synthetic urine.

In aspects wherein the absorbent body 24 includes the combination of hydrophilic fibers and high-absorbency particles, the hydrophilic fibers and high-absorbency particles can form an average basis weight for the absorbent body 24 that is within the range of about 400–900 grams per square meter. In certain aspects of the invention, the average composite basis weight of such an absorbent body 24 is within the range of about 500–800 grams per square meter, and preferably is within the range of about 550–750 grams per square meter to provide the desired performance.

To provide the desired thinness dimension to the various configurations of the absorbent article of the invention, the absorbent body 24 can be configured with a bulk thickness that is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or other forms that would serve the same purpose. In general, the high absorbency material is present in the absorbent body 24 in an amount of from about 5 to about 90 percent by weight, desirably in an amount of at least about 30 percent by weight, and even more desirably in an amount of at least about 50 percent by weight based on a total weight of the absorbent body 24. For example, in a particular aspect, the absorbent body 24 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrapsheet is typically placed about the absorbent body 24 over at least the two major facing surfaces thereof. The tissue wrapsheet can be composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers constituting the absorbent body 24.

The absorbent body 24 of the different aspects of the present invention further includes a plurality of zones of high air permeability which allow air and vapors to readily pass through the absorbent body 24 and through the vapor permeable outer cover 20 out of the diaper 10 into ambient air. For example, the absorbent body 24 may include a plurality of air passageways that provide the absorbent body 24 with zones or regions of high air permeability. The portions of the absorbent body 24 adjacent the air passageways provide zones or regions of high absorption. The zones of high air permeability are designed to provide the maximum air exchange from the absorbent body 24 while the zones of high absorption are designed to receive and hold the majority of the body exudates. The absorbent body 24 may define any number of zones of high air permeability that provide the improved air exchange. Desirably, the absorbent body 24 defines at least 3 and more desirably at least 5 different zones of high air permeability for improved performance.

The zones of high air permeability, such as the air passageways, are configured to enhance the breathability of the article to reduce the hydration of the wearer's skin during use without allowing excessive condensation of vapor, such as urine, on the garment facing surface of the outer cover 20. Such condensation of vapor on the outer surface of the diaper 10 can undesirably dampen the wearer's clothes. The zones of high air permeability are generally located in the area of the diaper over which air and vapor can transfer from the bodyside liner 22, through the absorbent body 24 and any other intervening layer or layers of material, and out the vapor permeable outer cover 20. For example, the zones of high air permeability may be located throughout the entire absorbent body 24 or may be selectively located in those regions of the absorbent body 24 that provide the maximum air exchange, such as the intermediate section 16 of the diaper 20. In a particular aspect, the zones of high air permeability are located in the front and intermediate sections 12 and 16, respectively, of the diaper 10 for improved air exchange.

The zones of high absorption, on the other hand, are not designed to transfer a high level of air and vapor from the interior of the diaper 10. Thus, the air exchange from the bodyside liner 22 of the diaper 10 to the outer cover 20 of the diaper and into the ambient atmosphere (exterior of the diaper 10) occurs generally through the absorbent body 24 in the zones of high air permeability. Some air exchange through the absorbent body 24 can also occur in the zones of high absorption to a limited degree. The zones of high air permeability may have any desired configuration including rectangular, circular, hourglass, oval, and the like, and may also include selected longitudinal or lateral strips or multiple regions which may be intermittently located.

The zones of high air permeability may have any desired dimensions that effectively provide improved air exchange while preventing excessive condensation of vapor from the absorbent body 24 through and onto the garment facing surface of the outer cover 20. Desirably, the zones of high air permeability may define a total area of from about 5 to about 75 percent, more desirably at least about 10 percent, even more desirably from about 10 to about 70 percent, and still more desirably from about 10 to about 60 percent of the total surface area of the absorbent body 24 of the diaper 10. For example, in a diaper 10 intended for use on a medium sized infant, the zones of high air permeability may define a total area of from about 6 to about 90 square centimeters.

When the total area of the zones of high air permeability is greater than the above amounts, the diaper 10 may exhibit an undesirable amount of condensation of vapor on the exposed, garment facing surface of the outer cover 20 undesirably resulting in a clammy feeling on the outer surface of the diaper 10. Whereas, when the total area of the zones of high air permeability is less than the above amounts, the diaper 10 may exhibit a low level of air exchange resulting in high levels of skin hydration that can undesirably lead to skin irritation and rash.

The zones of high air permeability of the absorbent body 24 of the diaper 10 are constructed to be substantially permeable to at least air and preferably permeable to water vapor. For example, the zones of high air permeability of the absorbent body 24 define a Frazier Porosity value which is at least about 10 percent, more desirably at least about 20 percent and even more desirably at least about 50 percent greater than the Frazier Porosity value of the zones of high absorption of the absorbent body 24. As used herein, the term "Frazier Porosity" refers to the value determined according to the Frazier Porosity Test described in U.S. Pat. No. 6,217,890 issued Apr. 17, 2001 to Paul et al. When the zones of high air permeability exhibit Frazier Porosity values less than those indicated above, the diaper 10 may exhibit a low level of air exchange resulting in high levels of skin hydration that can undesirably lead to skin irritation and rash.

The zones of high air permeability may be provided in a variety of ways. The zones of high air permeability may be integral portions of the absorbent body 24 of the absorbent article or may be provided by apertures, holes or open spaces in the absorbent body 24. For example, portions of the absorbent body 24 may be discontinuous or removed to provide the zones. Alternatively, the zones of high air permeability may be provided by portions of the absorbent body 24 that are constructed to absorb less fluid exudates thereby resulting in improved air flow through such portions in use. For example, portions of the absorbent body 24 may be void of or contain substantially less high-absorbency material than other portions of the absorbent body 24 to provide such improved air flow. Portions of the absorbent body 24 may otherwise be treated or coated with a solution that renders them hydrophobic to provide the zones of high air permeability in selected areas. In other alternative configurations, the zones of high air permeability may be provided by creating voids or holes in the absorbent body 24 and placing other materials having a higher air permeability than the absorbent body 24, such as those materials described below as being suitable for the surge management layer 34, in the holes or voids.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper 10 of the different aspects of the present invention may further include a porous, liquid-permeable layer of surge management material 34, as representatively illustrated in FIG. 1. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the diaper 10 positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbond web of synthetic fibers, such as polyolefin fibers. The surge management layer 34 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular aspect, the surge management layer 34 includes a hydrophobic, nonwoven material having a basis weight of from about 30 to about 120 grams per square meter.

For example, in a particular aspect, the surge management layer 34 may include a bonded-carded-web, nonwoven fabric that includes bicomponent fibers and that defines an overall basis weight of about 83 grams per square meter. The surge management layer 34 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

In the illustrated aspects, the surge management layer 34 is arranged in a direct, contacting liquid communication with the absorbent body 24. The surge management layer 34 may be operably connected to the bodyside liner 22 with a conventional pattern of adhesive, such as a swirl adhesive pattern. In addition, the surge management layer 34 may be operably connected to the absorbent body 24 with a conventional pattern of adhesive. The amount of adhesive add-on should be sufficient to provide the desired levels of bonding, but should be low enough to avoid excessively restricting the movement of liquid from the bodyside liner 22, through the surge management layer 34 and into the absorbent body 24.

The absorbent body 24 is positioned in liquid communication with surge management layer 34 to receive liquids released from the surge management layer 34, and to hold and store the liquid. In the shown aspect, the surge management layer 34 includes a separate layer that is positioned over another, separate layer including the absorbent body 24, thereby forming a dual-layer arrangement. The surge management layer 34 serves to quickly collect and temporarily hold discharged liquids, to transport such liquids from the point of initial contact and spread the liquid to other parts of the surge management layer 34, and then to substantially completely release such liquids into the layer or layers constituting the absorbent body 24.

The surge management layer 34 can be of any desired shape. Suitable shapes include for example, circular, rectangular, triangular, trapezoidal, oblong, dog-boned, hourglass-shaped, or oval. In certain aspects, for example, the surge management layer 34 can be generally rectangular-shaped. In the illustrated aspects, the surge management layer 34 is coextensive with the absorbent body 24. Alternatively, the surge management layer 34 may extend over only a part of the absorbent body 24. Where the surge management layer 34 extends only partially along the length of the absorbent body 24, the surge management layer 34 may be selectively positioned anywhere along the absorbent body 24. For example, the surge management layer 34 may function more efficiently when it is offset toward the front waist section 12 of the diaper 10. The surge management layer 34 may also be approximately centered about the longitudinal center line of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIG. 1, the diaper 10 may also include a ventilation layer 32 located between the outer cover 20 and the absorbent body 24. The ventilation layer 32 serves to facilitate the movement of air within and through the diaper 10 and prevent the outer cover 20 from being in surface to surface contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular aspect, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may include a bonded-carded-web, nonwoven fabric that includes bicomponent fibers and that defines an overall basis weight of about 83 grams per square meter. The ventilation layer 32 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the outer cover 20 and the absorbent body 24. In the illustrated aspects, the ventilation layer 32 is coextensive with the absorbent body 24. This allows for the maximum degree of air exchange with minimal dampness on the garment facing surface of the outer cover 20.

In the illustrated aspects, the ventilation layer 32 is arranged in a direct, contacting liquid communication with the absorbent body 24. The ventilation layer 32 may be operably connected to the outer cover 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the outer cover 20.

The ventilation layer 32 may further serve to quickly collect and temporarily hold discharged liquids, which pass through the absorbent body 24 and, in particular, through the zones of high air permeability within the absorbent body 24. The ventilation layer 32 may then transport such liquids from the point of initial contact and spread the liquid to other parts of the ventilation layer 32, and then substantially completely release such liquids into the layer or layers of the absorbent body 24.

In order to protect and improve the barrier properties of the diaper wearer's skin, a composition of the invention is applied to the bodyfacing surface 11 of the bodyside liner 22 of the diaper 10. The compositions of the invention are simplified (i.e. require fewer components) compared to conventional skin care compositions applied to absorbent articles. The compositions of the invention generally can include emollient(s) and stability enhancer(s). The compositions of the invention do not include compounds that previously have been understood to act as "immobilizing" or "solidifying" agents. The compositions can also include natural fats or oils and sterols or sterol derivatives. For example, the compositions of the invention may include from about 40 to about 99 percent by weight of one or more emollients; and from about 1 to about 40 percent by weight of one or more stability enhancers. The composition may include other ingredients as well. Ranges are used to describe the relative amounts of components in the compositions of the invention as well as to describe the relative physical properties of the compositions. These ranges are illustrative and one of skill in the art will recognize that the nature of the composition will dictate the various levels of components that must be used to achieve the intended benefit for the skin of the diaper wearer. The levels can be determined by routine experimentation in view of the disclosure provided herein.

The compositions of the invention can be in a variety of physical forms including emulsions, lotions, creams, ointments, salves, suspensions, gels or hybrids of these forms.

The emollients of the compositions act as lubricants to reduce the abrasiveness of the bodyside liner 22 to the skin and, upon transfer to the skin, help to maintain the soft, smooth and pliable appearance of the skin. Emollients are skin conditioning ingredients that help to soften, smooth, plasticize, lubricate, moisturize, improve the appearance of, improve the feel of and protect the skin. Suitable emollients that can be incorporated into the compositions include oils such as petroleum based oils, petrolatum, vegetable based oils, hydrogenated vegetable oils, animal oils, hydrogenated animal oils, mineral oils, natural or synthetic oils, alkyl dimethicones, alkyl methicones, alkyldimethicone copolyols, phenyl silicones, alkyl trimethylsilanes, dimethicone, lanolin and its derivatives, esters, branched esters, glycerol esters and derivatives, propylene glycol esters and derivatives, alkoxylated carboxylic acids, alkoxylated alcohols, fatty alcohols, triglycerides, alkyl hydroxystearates and mixtures of such compounds. The esters can be selected from, but are not limited to, cetyl palmitate, stearyl palmitate, cetyl stearate, isopropyl laurate, isopropyl myristate, isopropyl palmitate and mixtures thereof. Ethers such as eucalyptol, cetearyl glucoside, dimethyl isosorbicide polyglyceryl-3 cetyl ether, polyglyceryl-3 decyltetradecanol, propylene glycol myristyl ether and mixtures thereof can also be used as emollients. The fatty alcohols include octyldodecanol, lauryl, myristyl, cetyl, stearyl and behenyl alcohol and mixtures thereof. For example, a particularly well suited emollient is petrolatum. Other conventional emollients may also be added in a manner that maintains the desired properties of the compositions set forth herein.

To have good transfer to the skin of the diaper wearer, the compositions may include from about 40 to about 99 percent by weight, desirably from about 60 to about 95 percent by weight, and more desirably from about 75 to about 90 percent by weight of the emollient. In particular aspects, the emollient can be at least a minimum of about 40 percent by weight. The emollient can alternatively be at least about 60 percent, and optionally, can be at least about 75 percent to provide improved performance. In other aspects, the emollient can be not more than a maximum of about 99 percent by weight. The emollient can alternatively be not more than about 95 percent, and optionally, can be not more than about 90 percent to provide improved effectiveness. Previously, it was believed that compositions including large amounts of emollient would migrate away from or into the bodyside liner at an undesirable rate. The stability provided by the stability enhancers of the invention is sufficient to prevent migration of the emollient(s). Typically, compositions that include low amounts of emollient tend to provide less transfer to the wearer's skin.

One or more stability enhancers may be added to the composition to increase the meltpoint viscosity of the emollient(s), to help stabilize the formulation on the body-facing surface 11 of the bodyside liner 22 and, thereby, to reduce migration and improve transfer to the skin. Having viscosity at elevated temperatures prevents the compositions from migrating into or away from the materials to which they are applied. However, the stability enhancer component permits a low viscosity (greater than about 40 centipoise) under shear for the compositions at process conditions. Typically, process temperatures are approximately 5° C. above the melting point of the composition. Generally, the process temperature is about 60° C. or higher. Different compositions of the invention will have different melting points. The stability enhancers of the invention are capable of maintaining the viscosity of compositions of the invention up to temperatures just below the desired processing temperature for a given composition.

Examples of suitable stability enhancers include polyolefin resins, ethylene/vinyl acetate copolymers, natural clays, synthetic analogs of natural clays, organically modified clays, quaternary modified clays, quaternary starch compounds, polyethylene, silica, silica silylate, silica methyl silylate, colloidal silicone dioxide, magnesium aluminum silicate, polymethacrylate polymers, polystyrene copolymers and mixtures of these compounds. A particularly well suited viscosity enhancer is an ethylene/vinyl acetate copolymer commercially available from E. I. DuPont (Wilmington, Del.) under the trade designation "ELVAX".

To provide good stability on the bodyside liner 22, the compositions may include from about 1 to about 60 percent by weight, desirably from about 5 to about 40 percent by weight, and more desirably from about 10 to about 25 percent by weight of the stability enhancer. In particular aspects, the stability enhancer can be at least a minimum of about 1 percent by weight. The stability enhancer can alternatively be at least about 5 percent, and optionally, can be at least about 10 percent to provide improved performance. In other aspects, the stability enhancer can be not more than a maximum of about 60 percent by weight. The stability enhancer can alternatively be not more than about 40 percent, and optionally, can be not more than about 25 percent to provide good stability.

In another aspect, the compositions of the invention may include from about 0.1 to about 59 percent by weight of natural fats or oils. In such aspects, the compositions of the invention can include fats and oils that provide a source of essential and non-essential fatty acids similar to those found in the skin's natural barrier. Fats and oils include compounds that are fats, oils, essential oils, fatty acids, fatty alcohols, phospholipids and mixtures of such compounds. Fats and oils include oils derived from plant and animal sources. Similarly, the essential oils include essential oils derived from plant sources. Those of skill in the art would understand that all compounds commonly understood to have the structure of or to function as fats, oils, essential oils, fatty acids, fatty alcohols and phospholipids can be used as the natural fat or oil component of the composition of the invention. While an exhaustive list of each and every fat and oil that could be used in the compositions of the invention is not provided, those of skill in the art will understand and appreciate the individual compounds that can serve as a fat or oil component of the compositions of the invention.

Representative examples of fats and oils include, but are not limited to: Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, and Soybean Oil. Another suitable fat/oil for the compositions of the invention is PROLIPID 141 blend available from International Specialty Products of Wayne, N.J. The PROLIPID 141 blend is a mixture of glyceryl stearate, fatty acids, fatty alcohols and phospholipids.

In order to assist in replenishing skin barrier enhancing agents, the compositions of the invention may include fats and oils in an amount of from about 0.1 to about 59 percent by weight, desirably from about 5 to about 45 percent by weight, and more desirably from about 10 to about 30 percent by weight of the composition. In particular aspects, the fats and oils can be at least a minimum of about 0.1 percent by weight. The fats and oils can alternatively be at least about 5 percent, and optionally, can be at least about 10 percent to provide improved performance of the compositions. In other aspects, the fats and oils can be not more than a maximum of about 59 percent by weight. The fats and oils can alternatively be not more than about 45 percent, and optionally, can be not more than about 30 percent to provide improved effectiveness.

The compositions of the invention can also include sterols and sterol derivatives that act in combination with the natural fats/oils to provide natural skin barrier enhancement and skin barrier recovery. Sterols and sterol derivatives that can be used in the compositions of the invention include, but are not limited to: β-sterols having a tail on the 17 position and having no polar groups for example, cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, "AVOCADIN" (trade name of Croda Ltd of Parsippany, N.J.), sterol esters and similar compounds, as well as mixtures thereof. The compositions of the invention can include sterols, sterol derivatives or mixtures of both sterols and sterol derivatives in an amount of from about 0.1 to about 10 percent by weight, desirably from about 0.5 to about 5 percent by weight and more desirably from about 0.8 to about 1 percent by weight of the composition. In particular aspects, the sterols can be at least a minimum of about 0.1 percent by weight. The sterols can alternatively be at least about 0.5 percent, and optionally, can be at least about 0.8 percent to provide improved performance. In other aspects, the sterols can be not more than a maximum of about 10 percent by weight. The sterols can alternatively be not more than about 5 percent, and optionally, can be not more than about 1 percent to provide improved effectiveness.

If it is desired that the composition provide a treatment for the skin, the composition can also include an active ingredient such as a diaper rash skin protectant. Skin protectants are drug products that protect injured or exposed skin or mucous membrane surfaces from harmful or annoying stimuli. Suitable active ingredients, in addition to those mentioned above as suitable emollients, that can be incorporated into the composition include, but are not limited to, allantoin and its derivatives, aloe, aluminum hydroxide gel, calamine, cocoa butter, dimethicone, cod liver oil, glycerin, kaolin and its derivatives, lanolin and its derivatives, mineral oil, petrolatum, shark liver oil, talc, topical starch, zinc acetate, zinc carbonate, zinc oxide and the like, and mixtures thereof. The composition may include from about 0.10 to about 59 percent by weight of the active ingredient depending upon the skin protectant, the amount desired to be transferred to the skin or the amount of a particular skin protectant required in the U.S. Food and Drug Administration monograph.

In order to better enhance the benefits to the wearer, additional ingredients can be included in the compositions of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/organomodified silicones (protection, water resistance, lubricity, softness); oils (mineral, vegetable, and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

An important property of the compositions of the present invention is their ability to remain on the surface of the bodyside liner 22 and their resistance to migration into the diaper 10 such that they can readily be transferred to the wearer's skin. It is particularly desirable for the compositions to resist migration through the bodyside liner 22 toward the absorbent body 24. In this regard, the articles having the compositions of the present invention applied to their bodyside liner 22 define a z-direction migration loss of no more than about 55%, desirably no more than about 50%, more desirably no more than about 45%, even more desirably no more than about 40% and yet even more desirably no more than about 30% when subjected to the Z-Direction Lotion Migration Test described in U.S. Pat. No. 6,149,934 issued Nov. 21, 2000 to Krzysik et al. incorporated herein by reference. In articles that have a greater z-direction migration loss, the composition undesirably migrates into the interior and along the surface of the bodyside liner 22 and at times through the bodyside liner 22 into the absorbent body 24 of the article which results in a lower reduction in abrasion and less transfer to the skin of the wearer. Surprisingly, as will be shown herein, the compositions of the invention have z-direction migration loss values comparable—and sometimes even lower—than known compositions. This is surprising given that the compositions do not contain any immobilizing agents.

Moreover, to provide the improved stability and transfer to the skin of the wearer, the compositions of the present invention may define a melting point of from about 32° C. to about 100° C., desirably from about 35° C. to about 80° C., and more desirably from about 40° C. to about 75° C. Compositions that have lower melting points exhibit migration of the composition during use and at elevated temperatures in storage that can undesirably result in reduced transfer to the skin. Whereas, compositions that have higher melting points may require that the composition be at a temperature above the flash point of the bodyside liner 22 material which can undesirably lead to fires. The melting points of the compositions of the invention cause the compositions to be relatively stable and localized on the bodyfacing surface 11 of the diaper 10 at room temperature and readily transferable to the skin of the wearer at body temperatures. However, the compositions of the invention are not completely liquid under extreme storage conditions. Desirably, the compositions are easily transferable to the skin by way of normal contact, wearer motion, adhesion or body heat. When the compositions are relatively stabilized at room temperature, a lesser quantity of composition is required on the bodyfacing surface 11 to provide a beneficial effect.

The compositions of the present invention may further define a low shear viscosity at about 55° C. of greater than about 10,000 centipoise, desirably from about 50,000 to about 1,000,000 centipoise, and more desirably from about 100,000 to about 800,000 centipoise for reduced migration and improved transfer to the skin of the wearer. Compositions that have lower melt point viscosities may exhibit migration of the composition through the bodyside liner 22 into the absorbent body 24 of the article which can undesirably result in reduced transfer to the skin.

Further, the compositions of the present invention may also define a high shear viscosity of greater than about 40 centipoise, desirably from about 100 to about 500 centipoise, and more desirably from about 150 to about 250 centipoise at a temperature of about 60° C. (or higher temperatures depending on the components and melting point of the composition).

The penetration hardness of the compositions of this invention can be from about 2 to about 150 millimeters, more desirably from about 10 to about 90 millimeters, more desirably from about 40 to about 75 millimeters at 25° C. The hardness of the compositions of this invention is important for two reasons. First, the softer the formulation the more mobile the formulation will be, making the formulation more likely to migrate to the inner plies of the diaper 10, which is not desirable. Secondly, softer compositions tend to be more greasy/oily to the touch, which is also less desirable.

The composition may be applied to the entire bodyfacing surface 11 of the bodyside liner 22 or may be selectively applied to particular sections of the bodyfacing surface 11, such as the medial section along the longitudinal centerline of the diaper 10, to provide greater lubricity of such sections and to transfer such composition to the wearer's skin. Alternatively, the bodyfacing surface 11 of the bodyside liner 22 may include multiple stripes of the composition applied to it. For example, the bodyfacing surface 11 of the bodyside liner 22 may include from 1 to 20 stripes of composition extending along the longitudinal direction of the diaper 10. The stripes may extend the full length of the bodyside liner 22 or only a portion thereof. The stripes may also define a width of from about 0.2 to about 1 centimeters.

The composition should cover a sufficient amount of the bodyfacing surface 11 of the bodyside liner 22 to ensure adequate transfer to the skin and reduced abrasion between the bodyside liner 22 and the wearer's skin. Desirably, the composition is applied to at least about 5 percent and more desirably at least about 25 percent of the bodyfacing surface 11 of the bodyside liner 22.

The composition can be applied to the bodyside liner 22 at any add-on level that provides the desired transfer benefit. For example, the total add-on level of the composition can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the composition on the skin barrier function and the specific composition. As discussed above, the good stability and reduced tendency to migrate of the compositions of the present invention allows a lesser amount of composition to be applied to the bodyside liner 22 to achieve the same benefit when compared with conventional compositions.

The composition may be applied to the bodyside liner 22 in any of many well known manners. A preferred method to uniformly apply the composition to the bodyfacing surface 11 of the bodyside liner 22 is spraying or slot coating. Spraying or slot coating the composition is the most exact process and offers maximum control of the composition distribution and transfer rate. However, other methods, such as rotogravure or flexographic printing and foam application can be used. The compositions of the present invention can be applied after the bodyfacing material has been incorporated into the absorbent article or prior to incorporating the body facing material into the absorbent article.

The composition may be applied to the bodyside liner 22 by (a) heating the composition to a temperature above the melting point of the composition, causing the composition to melt, (b) uniformly applying the melted composition to the bodyfacing surface 11 of the bodyside liner 22; and (c) resolidifying the composition applied to the bodyfacing surface 11. Desirably, resolidification of the composition occurs almost instantaneously, without the need for external cooling devices such as chill rolls. This can occur if the composition is heated to a temperature only slightly above or at the melting point of the composition. However, external cooling devices such as chill rolls, either before or after the application of melt, can be used if desired to accelerate resolidification. Other cooling methods such as cooling tunnels could also be used.

The increased viscosity of the composition at the process temperature and the instantaneous resolidification tends to impede penetration of the composition into the bodyside liner 22 and absorbent body 24 of the diaper 10 and retain it on the bodyfacing surface 11 of the bodyside liner 22, which is advantageous. For example, the temperature of the melted composition can advantageously be less than about 10° C., more desirably less than about 5° C., and still more desirably less than about 2° C. above the melting point of the composition prior to applying it to the bodyside liner 22 for reduced migration. As the temperature of the melted composition approaches the freezing point of the composition, the viscosity of the melted composition generally increases, which further enhances the tendency of the melted composition to be retained on the bodyfacing surface 11.

As described herein, viscosity, penetration hardness and melting point contribute to how stable a composition will be on a nonwoven substrate, such as a bodyside liner 22. Surprisingly, the compositions of the invention have properties comparable to the properties of previously known compositions even though the compositions of the invention do not include an immobilizing agent. While all of the compositions of the invention have good stability, in some cases, the compositions even have better stability than previously known compositions. In order to demonstrate the stability of the present compositions, the compositions described in Table 1. below were prepared and evaluated. Two previously known compositions were also prepared for comparison.

TABLE 1

Formula Composition (components given in percentages by weight)

| | |
|---|---|
| A | 50% White Petrolatum (White Protopet 1S obtained from Witco-Crompton) |
| | 35% Cetearyl Alcohol (obtained from Glenn Corp.) |
| | 15% Steareth-2 (obtained from ICI Specialty Chemicals) |
| | (described as Example 5 at Col. 22, lines 1–24 of U.S. Pat. No. 5,643,588 issued July 1, 1997 to Roe et al.)[Ie |
| B | 60% Snow White Petrolatum (available from Penreco) |
| | 34% Wax Blend (ozokerite wax available from International Group, Inc.) |
| | 6% ELVAX 410 resin (available from E.I. DuPont) |
| | (ointment provided on HUGGIES diapers sold by Kimberly-Clark Corporation) |
| C | 90% White Petrolatum USP (available as Blend 4554 from Penreco) |
| | 10% ELVAX 410 resin |
| D | 90% White Petrolatum USP (available as Blend 4554 from Penreco) |
| | 10% ELVAX 205 resin (available from E.I. DuPont) |
| E | 61% White Petrolatum USP (available as Blend 4554 from Penreco) |
| | 39% ELVAX 220 resin (available from E.I. DuPont) |
| F | 79% White Petrolatum USP (available as Blend 4554 from Penreco) |
| | 21% ELVAX 220 resin (available from E.I. DuPont) |

TABLE 1-continued

Formula Composition (components given in percentages by weight)

| | |
|---|---|
| G | 95% White Petrolatum USP (available as Blend 4554 from Penreco) |
| | 5% ELVAX 220 resin (available from E.I. DuPont) |
| H | 97% White Petrolatum USP (available as Blend 4554 from Penreco) |
| | 3% ELVAX 220 resin (available from E.I. DuPont) |
| I | 98% White Petrolatum USP (available as Blend 4554 from Penreco) |
| | 2% ELVAX 220 resin (available from E.I. DuPont) |
| J | 99% White Petrolatum USP (available as Blend 4554 from Penreco) |
| | 1% ELVAX 220 resin (available from E.I. DuPont) |

Penreco is located in Karns City, Pennsylvania; Witco-Crompton Corp. is located in Petrolia, Pennsylvania; E.I. DuPont is located in Wilmington, Delaware; Glenn Corp. is located in St. Paul, Minnesota; ICI Specialty Chemicals is located in Wilmington, Delaware; and International Group, Inc. is located in Wayne, Pennsylvania.

Formulas A and B are previously known formulas and formulas C–J are compositions of the invention. The ELVAX resins used in the compositions of Table 1. are suitable stability enhancers. The ELVAX resins differ in their ratios of vinyl acetate to ethylene. Two hundred series resins are 28% by weight vinyl acetate and 400 series resins are 18% by weight vinyl acetate.

Figure 2:
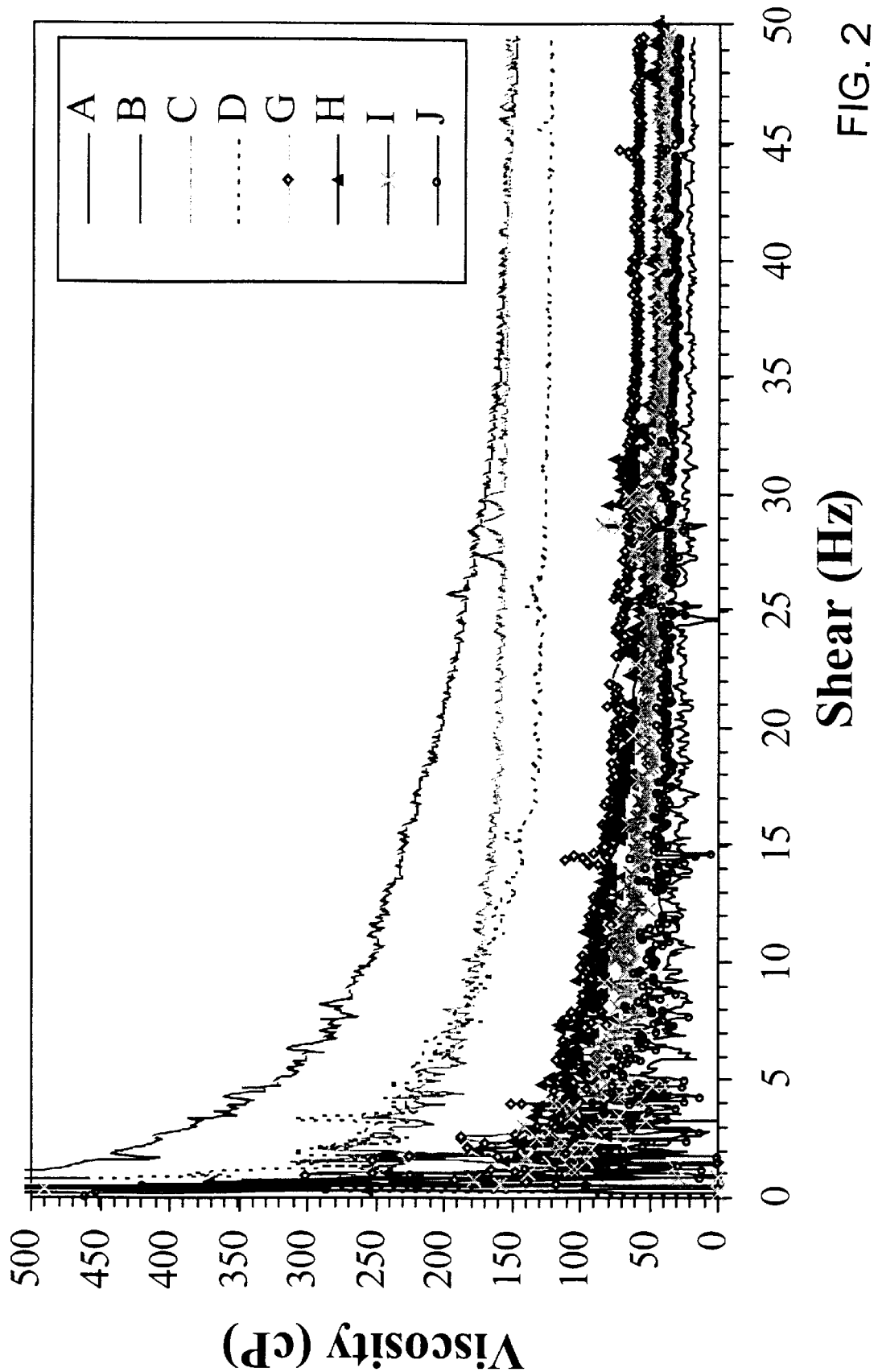
FIG. 2 graphically represents the relationship between viscosity and shear rate for compositions of the invention and previously known compositions.
Figure 3:
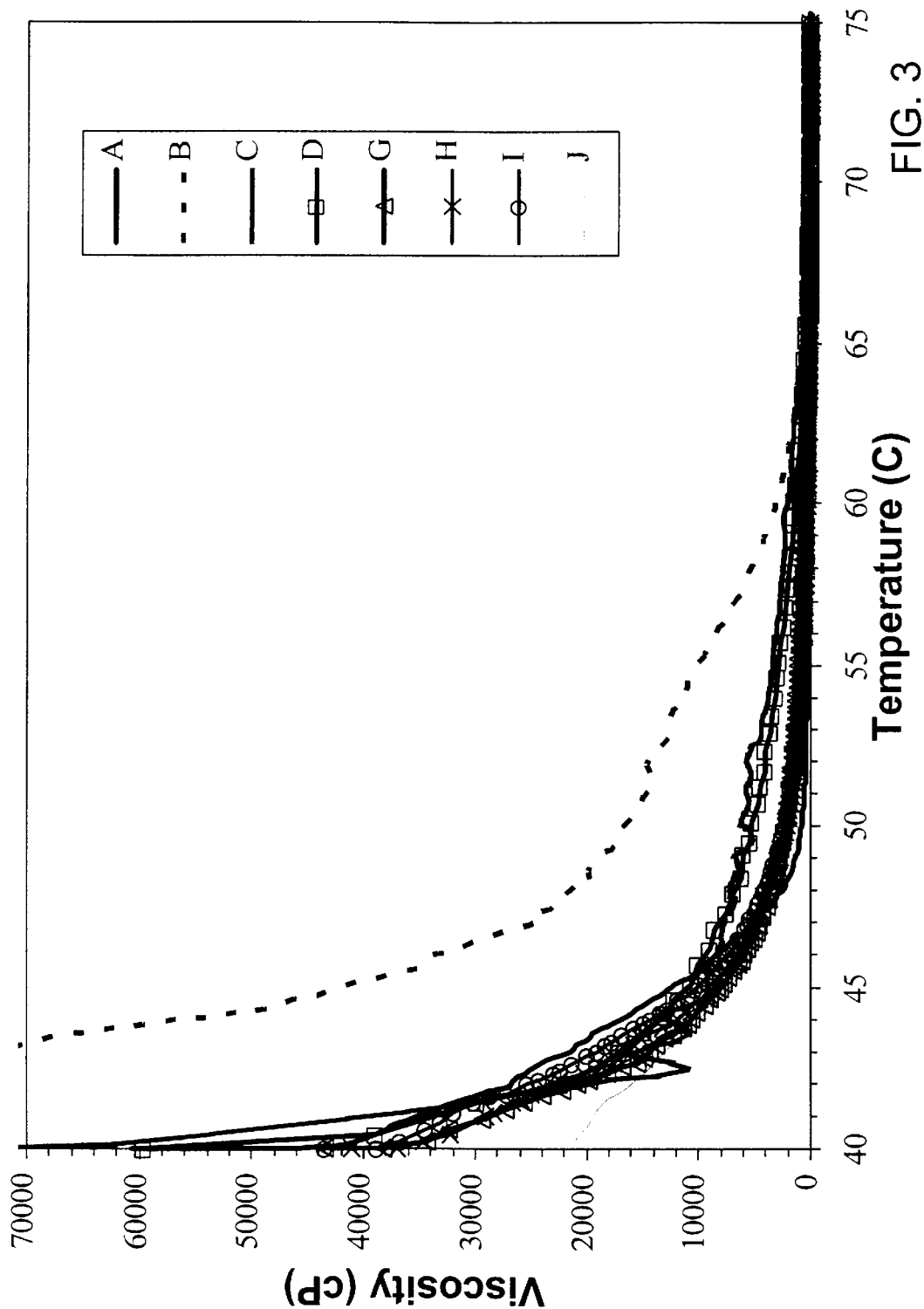
FIG. 3 graphically represents the relationship between viscosity and temperature for compositions of the invention and previously known compositions.

As described herein, the viscosity of a composition is relevant to how stable the composition is on a bodyside liner 22. The viscosity of each of the formulas was measured. The viscosity measurements were performed using a RheoStress 1 rheometer with a C35/4Ti cone and plate head, available from Thermo Haake located in Paramus, N.J. The viscosity of the compositions was measured as the shear rate and then separately, the temperature was ramped. The shear rate/temperature ramps were from the lowest to highest value, then returning to the starting point, consecutively. For the viscosity as a function of shear rate measurements, the temperature was held constant at 75° C. The shear rate ramp was from 0.001 Hz to 100 Hz, then back to 0.001 Hz. Both the increasing and decreasing ramps lasted 240 seconds and collected 900 data points apiece. For the viscosity as a function of temperature measurements, the shear rate was held constant at 15.84 Hz. The temperature ramp was from 40° C. to 95° C., then back to 40° C. Both the increasing and decreasing ramps lasted 300 seconds and collected 300 data points apiece. The temperature ramp was 0.1833° C./sec with no equilibration time programmed in, i.e. a ramp not a step system. The compositions behaved similarly over the shear rate ramp as shown in FIG. 2. The compositions also behaved similarly over the temperature ramp as shown in FIG. 3.

Figure 4:
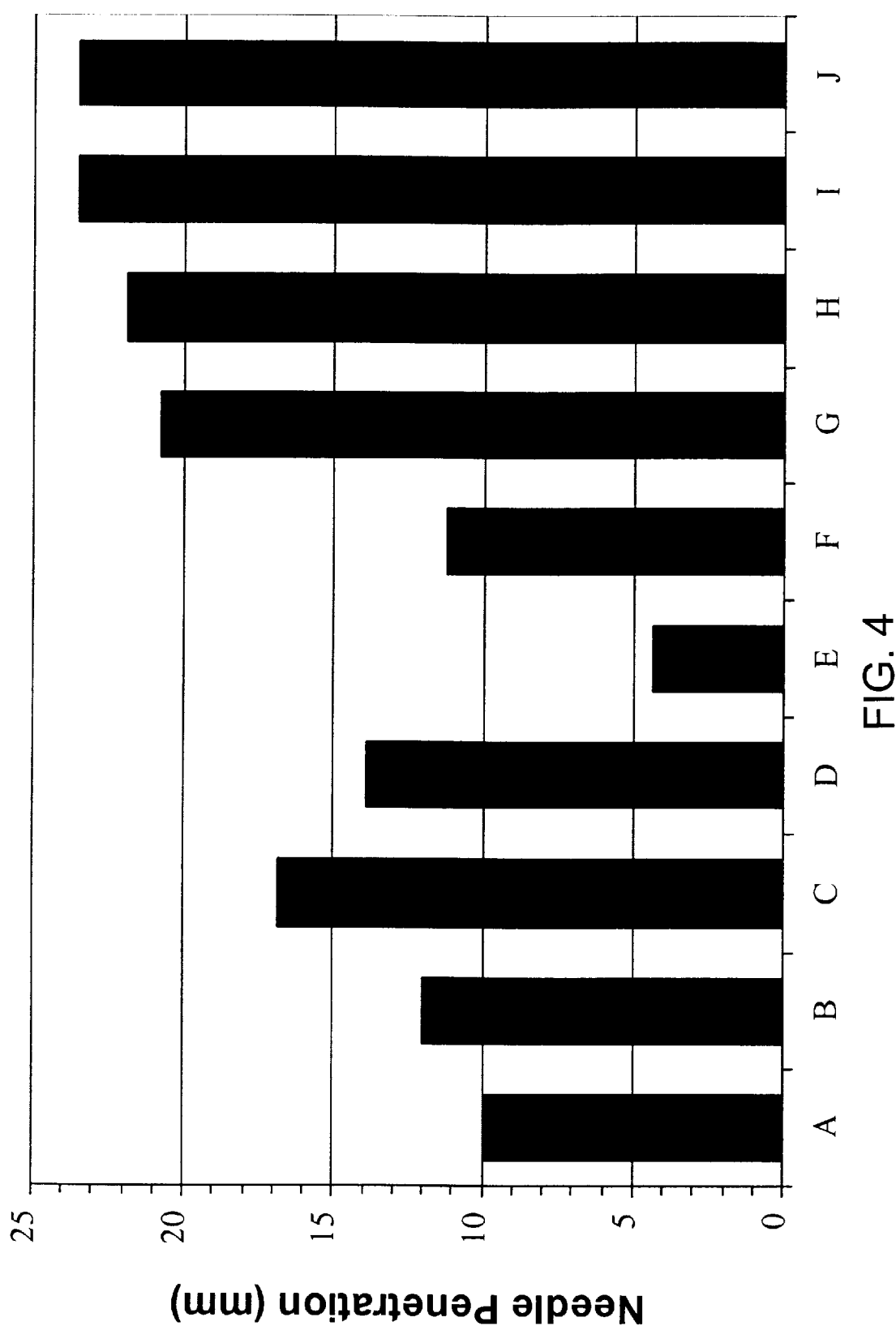
FIG. 4 graphically represents the penetration hardness for compositions of the invention and previously known compositions.

The compositions described in Table 1. were also evaluated for their hardness. The "hardness" of a composition is measured by taking needle penetration measurements. The needle penetration measurements for the compositions of Table 1. were collected on a Scientific Petroleum Instruments Precision Penetrometer. The needle penetration measurements were made at 25° C. using an H1312 needle and a 50 gram weight, for 5 seconds. This procedure is a modification to ASTM method D1321. As shown in FIG. 4, the compositions of the invention have penetration hardnesses comparable to the previously available compositions. Even formula "J", having the lowest amount of stability enhancer, had a penetration hardness of less than 25 mm.

The compositions described in Table 1. were also evaluated for their stability on a standard bodyside liner 22 of a diaper 10. The ten compositions were slot coated onto standard bodyside liner material (0.5 ounces/yd$^2$ polypropylene spunbond). The targeted add-on was 0.32 grams for an area of material equivalent to what would be used in a Step 3 size HUGGIES ULTRATRIM diaper. The slot coating temperature was 85° C., except for formula "E" for which the temperature was 98.8° C. Twenty pieces of coated liner (43.5 cm long by 27.1 cm wide) were obtained for each composition. Half of the liner samples were used to determine the amount of ointment applied to the liner prior to aging. The other half were used in the fabrication of diapers to investigate the retention of the compositions on the bodyside liner material under accelerated aging conditions.

The liner samples used to determine the initial add-on of composition were put into plastic, sealable bags and tested using a Dionex accelerated solvent extractor (ASE 200). Dionex Corporation is located in Sunnyvale, Calif. The liner samples being used for accelerated aging were placed onto diapers and stored at 40° C. and 75% RH (relative humidity) for seven days. In order to simulate the environment of the diapers as sold in the bag, it was determined that 15 lbs. of force (0.029 kg/cm$^2$) are applied to a stack of diapers. The diapers were then placed into four stacks of 25 diapers in resealable plastic bags and a piece of plastic with a surface area of 1023.5 cm$^2$ was placed on top of the diapers. To model the pressure the diapers experience in a bag, a total of 29.7 kg including the weight of the plastic, was applied to the diapers.

Figure 5:
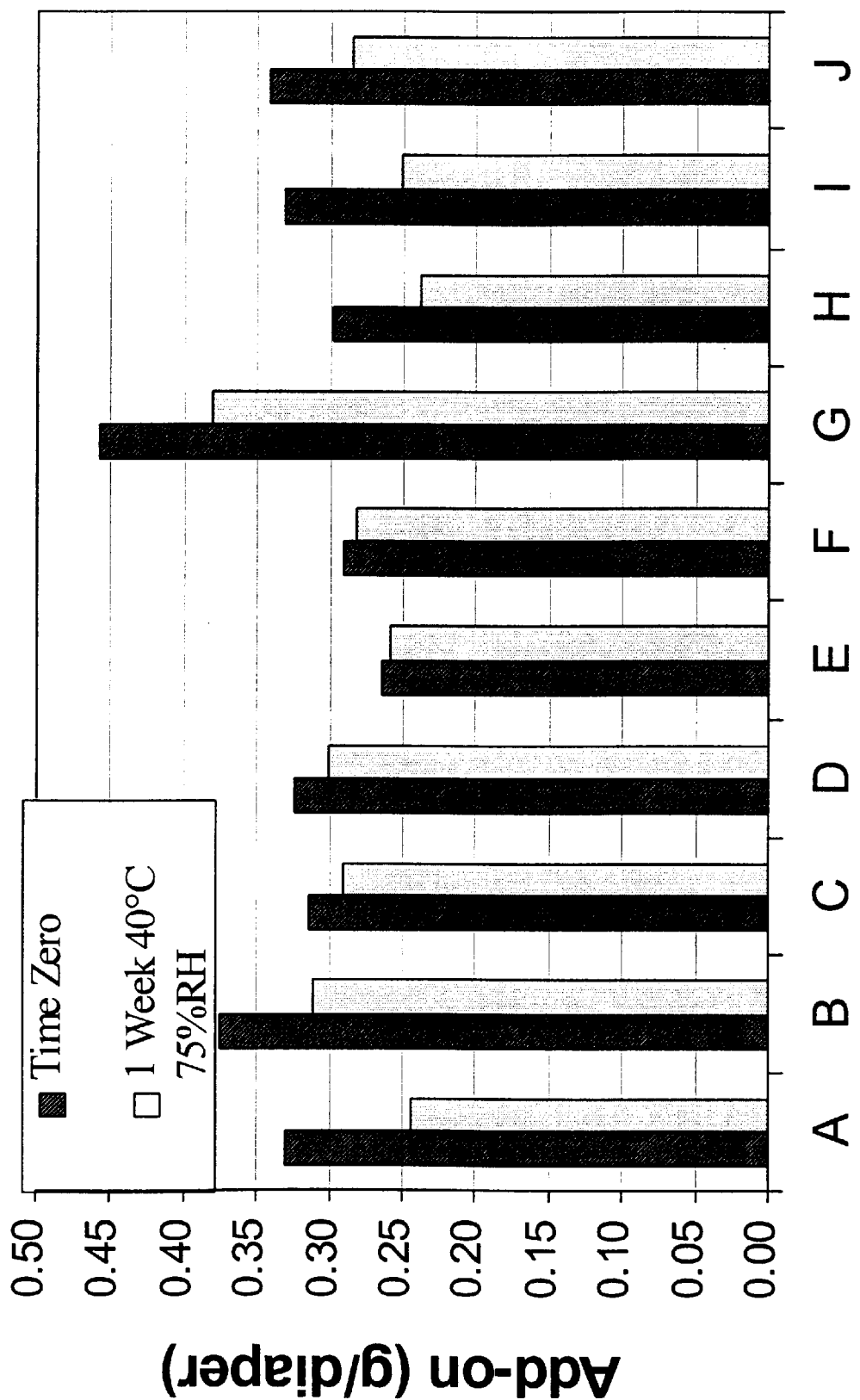
FIG. 5 graphically represents the "add-on" amount of composition extracted from liner material both before and after aging for compositions of the invention and previously known compositions.

Once the diapers had been prepared, they were placed into aging chambers at 40° C. and 75% RH for seven days. After aging, each liner sample was extracted individually in an 11 cm cell with chloroform. Eighteen liner samples without any composition were extracted to get a background reading on the liner material. The average of the blanks was subtracted from each sample to correct for the background level of extractables. The extracts were evaporated for 60 minutes at 60° C. and left uncapped in a fume hood overnight to remove all of the chloroform. The extraction sample vials were weighed after a 60 minute cycle as well as the next day to check for additional chloroform loss. The relative quantities of ointment, extracted from the liner material both before and after aging, are shown in FIG. 5. "Percent Loss" from the liner—which is indicative of the Z-direction migration of a composition—can be calculated from the before and after "add-on" values. Percent loss is calculated as:

$$\% \text{ Loss} = 100 \cdot \frac{(\text{add} - \text{on}_{initial}) - (\text{add} - \text{on}_{final})}{(\text{add} - \text{on}_{initial})}$$

The percent loss values for the compositions tested are reported in Table 2. below.

TABLE 2

| Formula | % Loss at 40° C. |
|---|---|
| A | 26.2 |
| B | 17.3 |
| C | 7.5 |
| D | 7.2 |
| E | 2.5 |
| F | 3.3 |
| G | 16.9 |
| H | 20.4 |
| I | 24.0 |
| J | 16.6 |

The compositions of the invention demonstrated Percent Loss values comparable to the values for the previously known compositions, and in some cases, a lower Percent Loss. The low Percent Loss values were obtained for the compositions having higher quantities of a stability enhancer. Surprisingly, even the compositions containing low levels of stability enhancer (5% and less) did not experience Percent Loss greater than the previously known compositions.

The compositions of the invention contain fewer components than previously known compositions designed for application to absorbent articles; specifically, the compositions do not contain "immobilizing agents". Despite not containing any immobilizing agents, the compositions of the invention still possess physical properties comparable to previously known compositions. In particular, the compositions of the invention have good stability on a bodyside liner material. While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. An absorbent article comprising:

(a) an outer cover;

(b) a liquid permeable bodyside liner that defines a bodyfacing surface and that is connected in superposed relation to the outer cover;

(c) an absorbent body that is located between the bodyside liner and the outer cover; and (d) a composition on at least a portion of the bodyfacing surface of the bodyside liner that includes from about 40 to about 90 percent by weight of an emollient, from about 10 to about 60 percent by weight of a stability enhancer and not including an immobilizing agent wherein the composition has a percent loss of less than about 10 percent.

2. The absorbent article of claim 1, wherein the composition has a high shear viscosity less than about 20,000 centipoise at a temperature greater than about 60° C. and has a low shear viscosity greater than about 20,000 centipoise at a temperature of about 40° C.

3. The absorbent article of claim 1, wherein the emollient of the composition is selected from petrolatum; partially hydrogenated vegetable and animal oils; fatty add esters having a melting point greater than 30° C.; alkyl silicones having a melting point greater than 30° C.; lanolin: triglycerides having a melting point greater than 30° C. and mixtures thereof.

4. The absorbent article of claim 1, wherein the stability enhancer of the composition is selected from polyolefin resins, ethylene/vinyl acetate copolymers, polyethylene, silica, silica silylate, silica methyl silylate, alkyl hydroxy ethyl cellulose, quaternary starch compounds, natural clays, synthetic analogs of natural clays, organically modified clays, quaternary modified clays, colloidal silicone dioxide, magnesium aluminum silicate, polymethacrylate polymers, polystyrene copolymers and mixtures thereof.

5. The absorbent article of claim 1 wherein the composition further includes from about 0.1 to about 40 percent by weight of natural fats or oils.

6. The absorbent article of claim 5, wherein the natural fat or oil is selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

7. The absorbent article of claim 1 wherein the composition further includes from about 0.1 to about 10 percent by weight of sterols or sterol derivatives.

8. The absorbent article of claim 7, wherein the sterol or sterol derivative is selected from cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

9. The absorbent article of claim 1, wherein the composition has a penetration hardness of from about 2 millimeters to about 150 millimeters at 25° C.

10. The absorbent article of claim 1, wherein the composition further includes an active ingredient selected from allantoin and its derivatives, aloe, aluminum hydroxide gel, calamine, cocoa butter, cod liver oil, dimethicone, glycerin, kaolin and its derivatives, lanolin and its derivatives, mineral oil, petrolatum, white petrolatum, shark liver oil, talc, topical starch, zinc acetate, zinc carbonate, zinc oxide and mixtures thereof.

* * * * *